United States Patent [19]

Abidin et al.

[11] Patent Number: 5,352,220
[45] Date of Patent: Oct. 4, 1994

[54] GUARDED SKIN HOOK FOR SURGICAL PURPOSES AND METHOD THEREOF

[75] Inventors: Michael R. Abidin; Steven P. Lehmbeck, both of Baltimore, Md.

[73] Assignee: Leonard Bloom, Towson, Md.; a part interest

[21] Appl. No.: 56,030

[22] Filed: Apr. 30, 1993

Related U.S. Application Data

[63] Continuation-in-part of Ser. No. 867,881, Apr. 13, 1992, Pat. No. 5,222,951.

[51] Int. Cl.$^5$ .................. A61B 17/00; A61B 19/00
[52] U.S. Cl. .......................... 606/1; 128/20; 30/162
[58] Field of Search .............. 128/20; 604/159-162, 604/197, 198, 210; 606/1, 167, 172, 182, 190; 30/129, 137, 143, 151, 159, 162, 164.7, 322, 323, 329, 333, 340; 7/161; 433/116, 141, 146

[56] References Cited

U.S. PATENT DOCUMENTS

| | | | |
|---|---|---|---|
| 309,863 | 12/1884 | McGovern | 30/162 |
| 338,612 | 3/1886 | Pusey | 30/162 |
| 470,777 | 3/1889 | Billings | 30/162 |
| 734,590 | 7/1903 | Minnich | 30/162 |
| 2,873,522 | 2/1959 | Homola | 30/129 |
| 3,857,386 | 12/1974 | Ashbell | 128/20 |
| 3,904,033 | 9/1975 | Haerr | 30/164.7 |
| 4,682,981 | 7/1987 | Suzuki et al. | 604/158 |
| 5,071,426 | 12/1991 | Dolgin | 606/167 |

OTHER PUBLICATIONS

Borders Safety Skin Hooks–Catalogue–Smith and Nephew Richards pp. 3–4.

Primary Examiner—Stephen C. Pellegrino
Assistant Examiner—Glenn Dawson
Attorney, Agent, or Firm—Leonard Bloom

[57] ABSTRACT

A surgical skin hook (11, 100) has a guard (12, 105) that may be advanced to cover the prongs or hooks (14, 103) or retracted to expose the prongs or hooks (14, 103) for use during 5 a surgical procedure. In its advanced or closed position, the guard (12, 105) prevents accidental contact with the hooks (14, 103) thereby preventing nicks or cuts and the risks associated with contracting infectious diseases, such as AIDS. An improved method of using the guarded skin hook involves clamping the patient's skin (129) between the guard (105) and the hook or hooks (103) such that the skin (129) will not inadvertently fall off of the hook or hooks (103) as the skin (129) is peeled or lifted away from an incision (128) previously made on the patient.

29 Claims, 17 Drawing Sheets

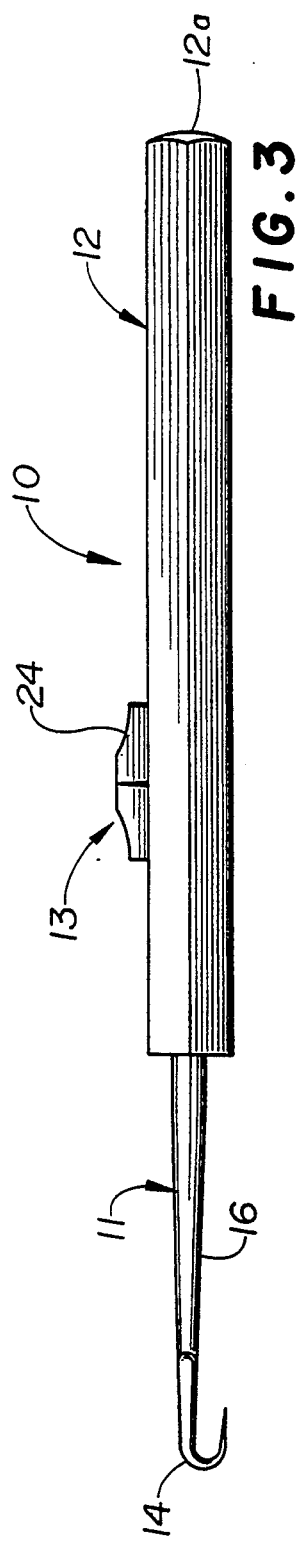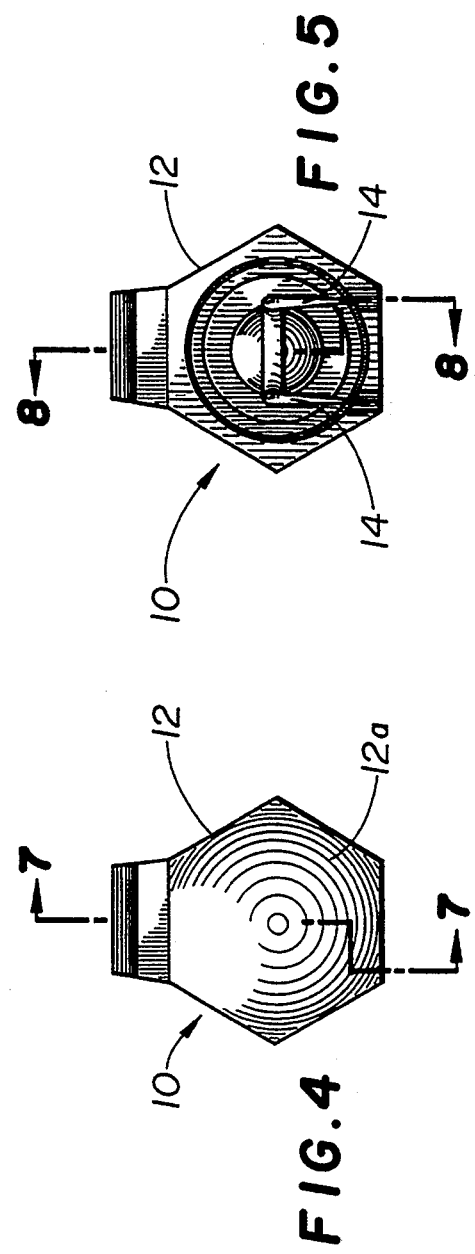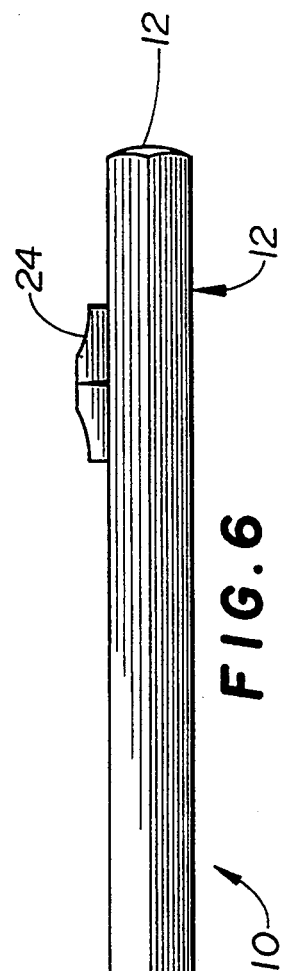

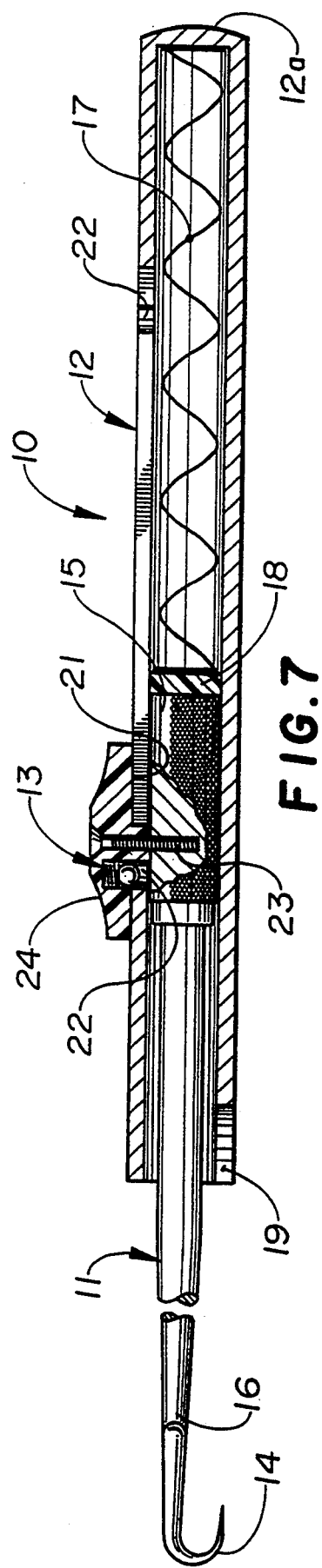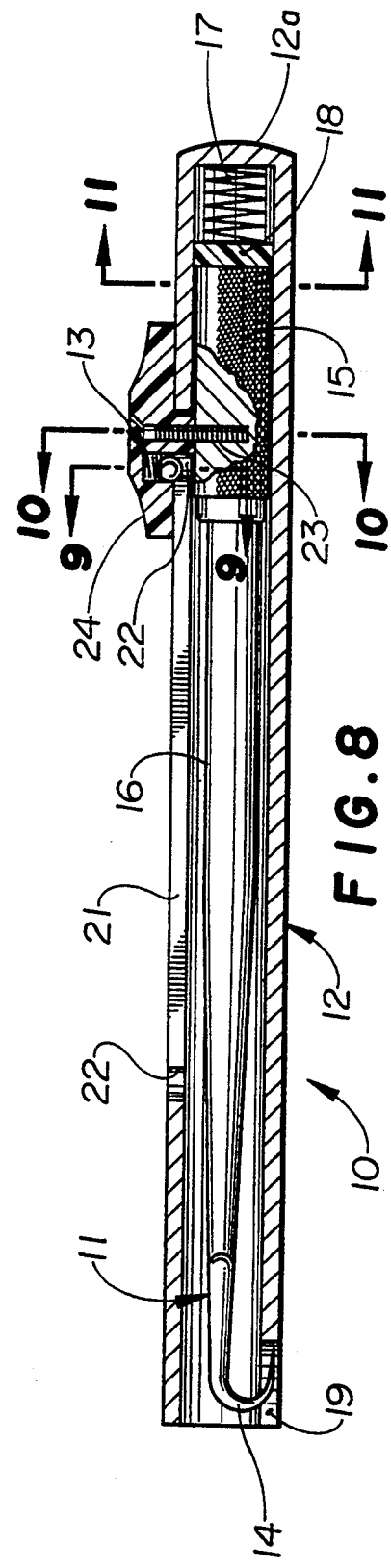

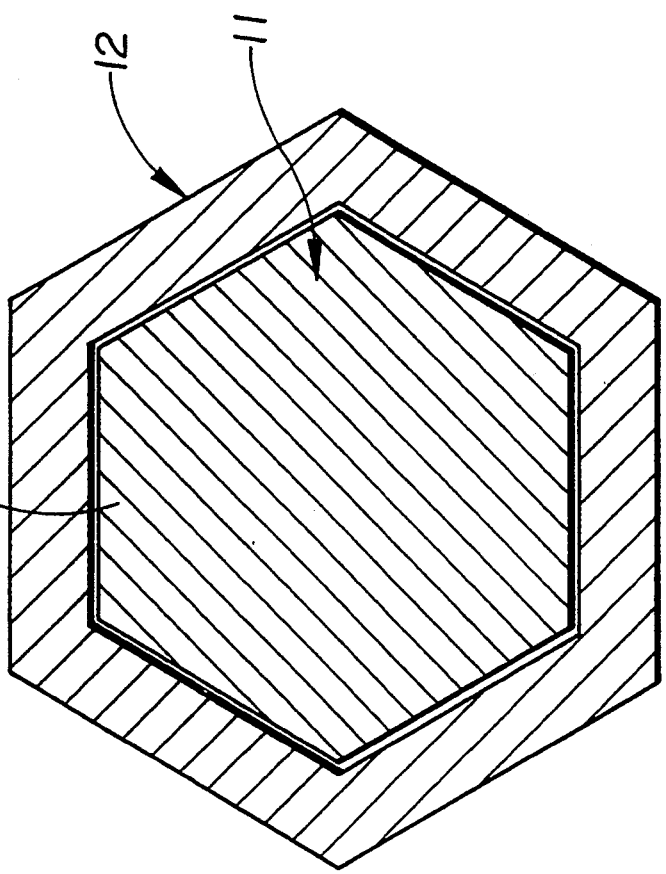
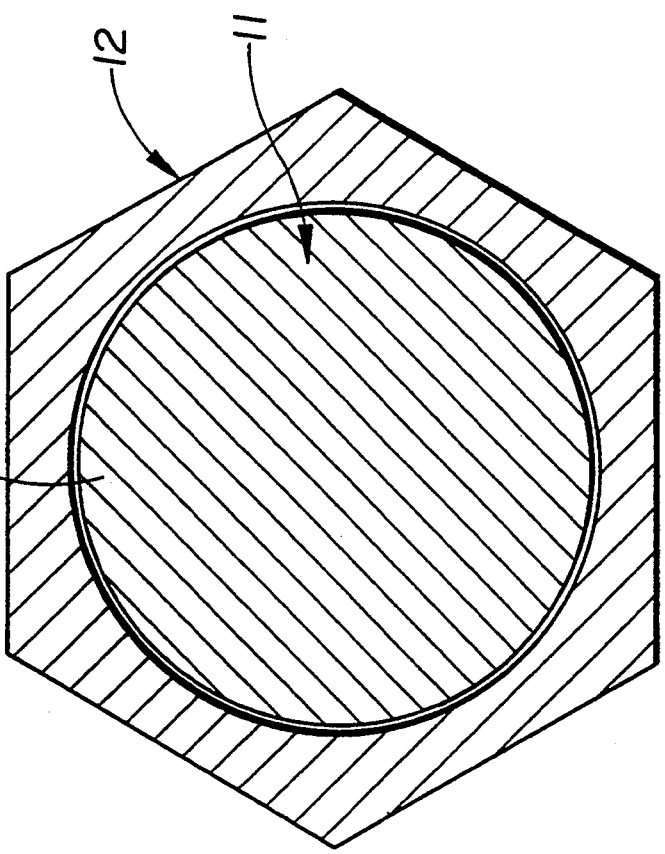

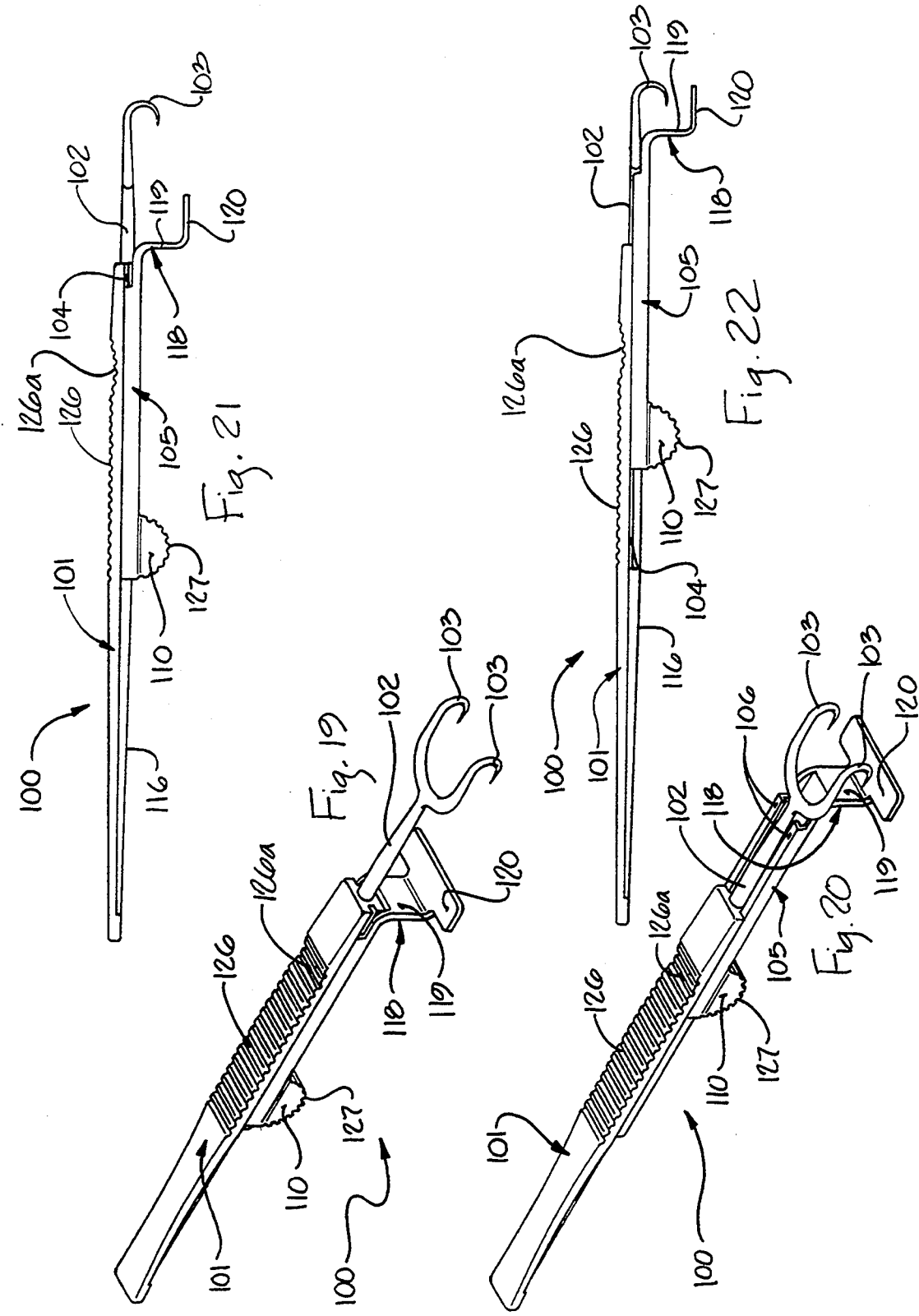

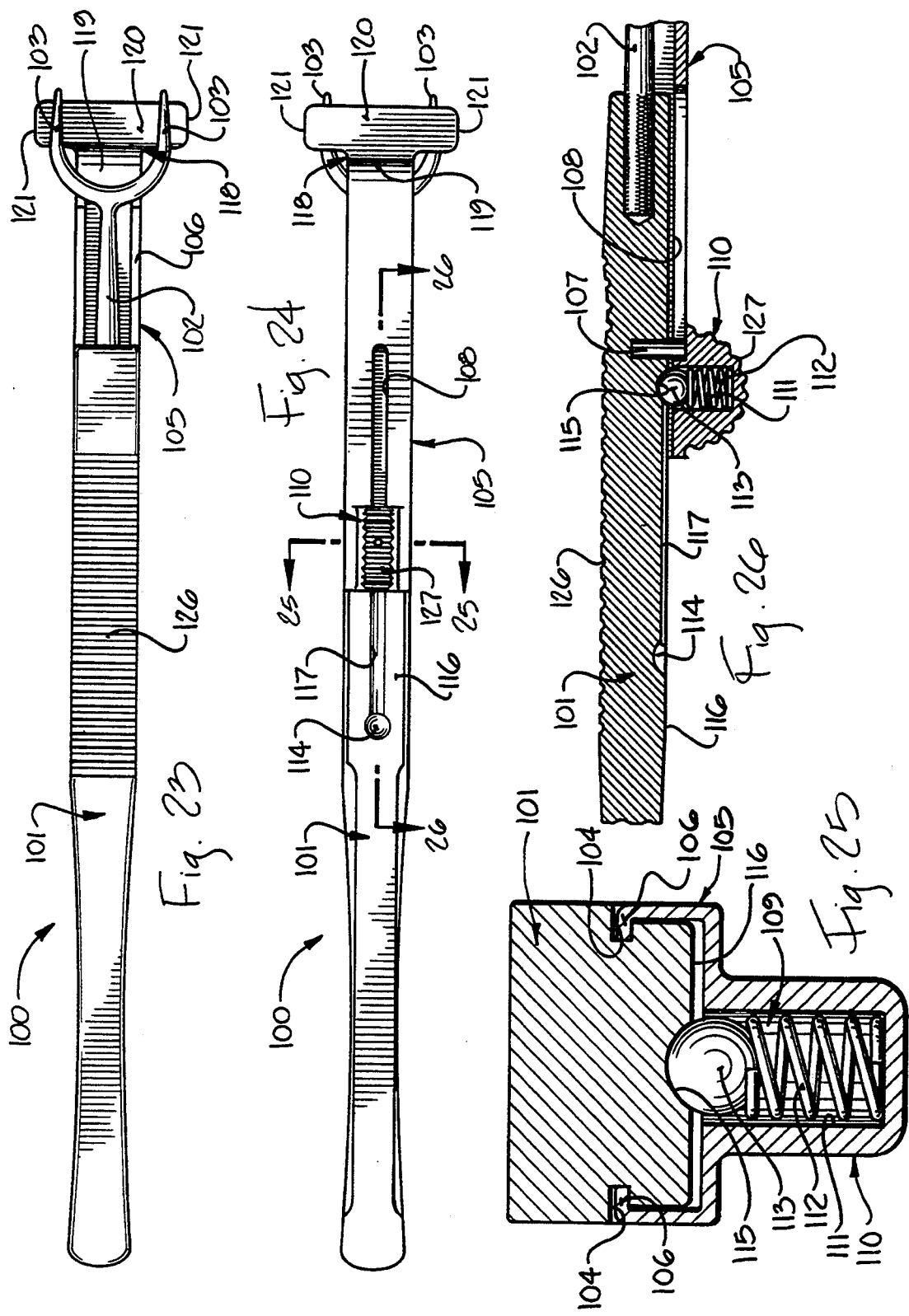

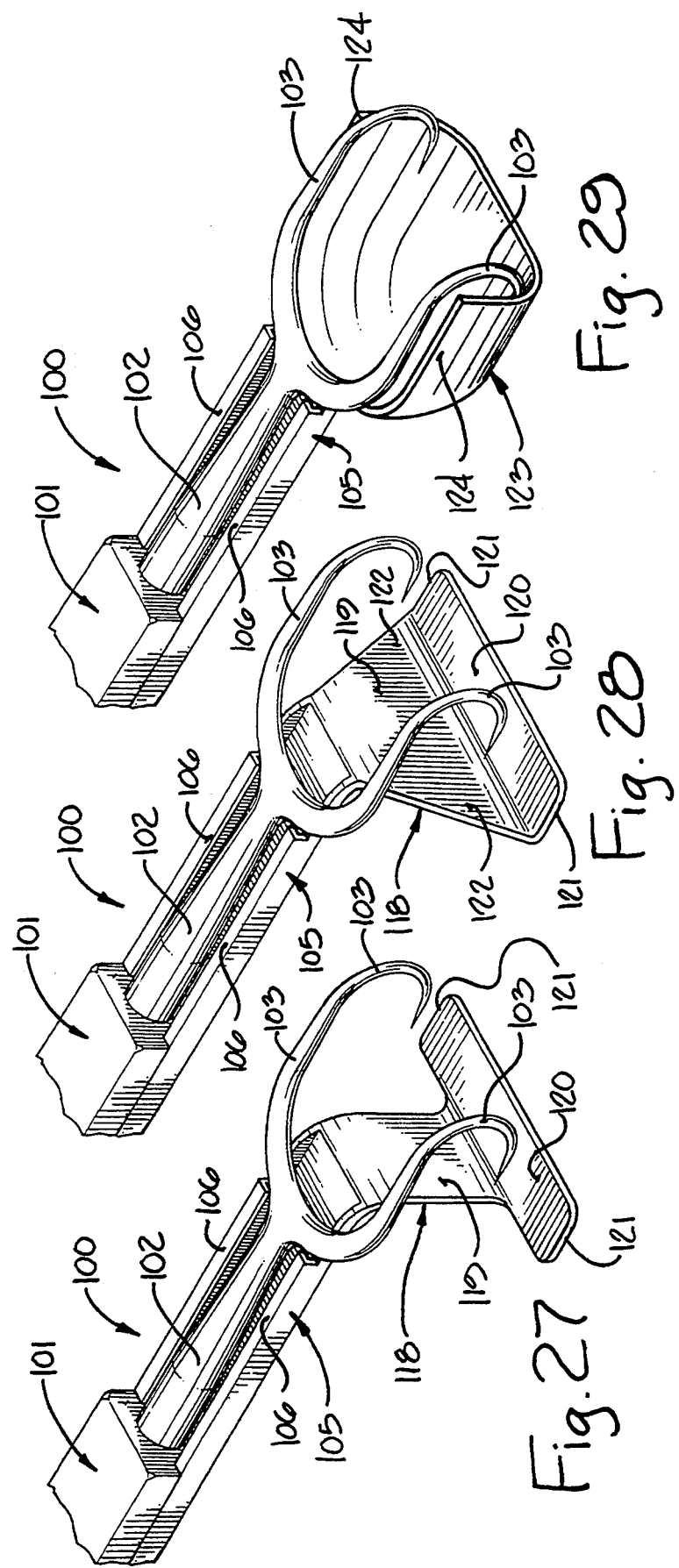

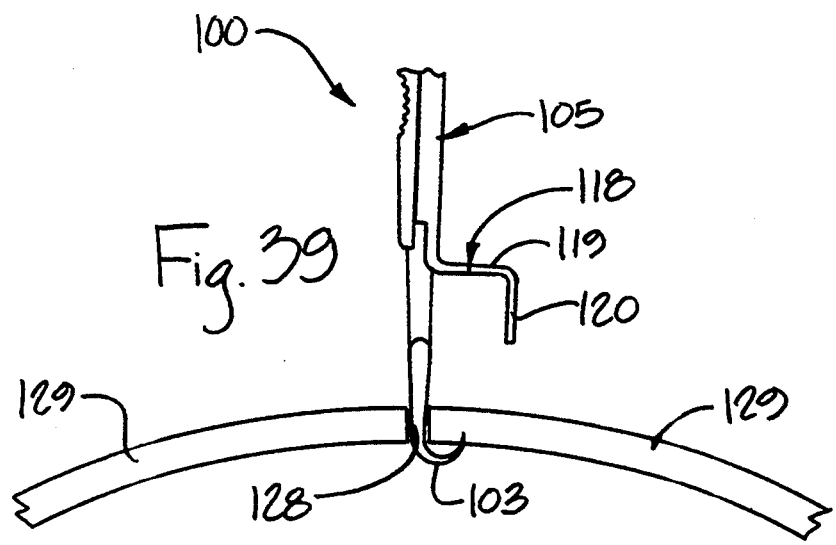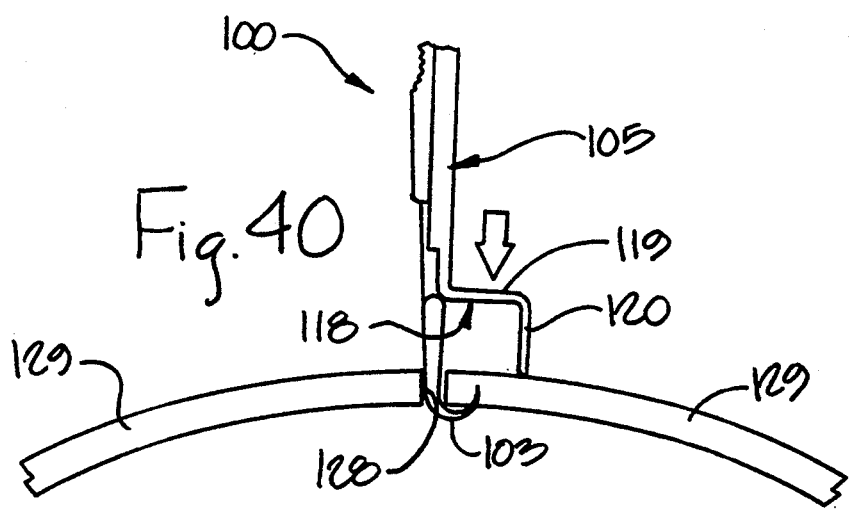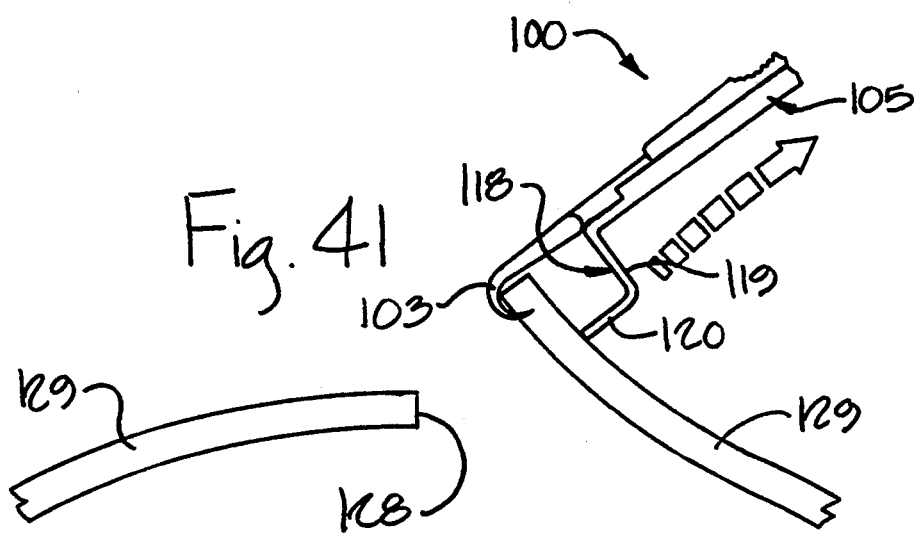

GUARDED SKIN HOOK FOR SURGICAL PURPOSES AND METHOD THEREOF

CROSS-REFERENCE TO RELATED APPLICATION

The present application is a continuation-in-part of U.S. patent application, Ser. No. 867,881 filed Apr. 13, 1992, entitled "GUARDED SKIN HOOK FOR SURGICAL USE", and now U.S. Pat. No. 5,222,951 issued on Jun. 29, 1993 the disclosure of which is hereby incorporated herein in its entirety.

FIELD OF THE INVENTION

The present invention relates to skin hooks for surgical purposes and, in particular, to a guarded skin hook and method of use thereof.

BACKGROUND OF THE INVENTION

Conventional skin hooks are used by surgeons and other health care professionals for pulling back and holding the patient's skin along an incision previously made during a surgical procedure. These skin hooks are unguarded, and their prongs or hooks are exposed at all times. The only covers provided for such conventional skin hooks are "one-use" covers, such as frangible plastic sheaths, that are torn or otherwise removed from the skin hooks before their use.

During routine surgical procedures, the operating room assistant (such as a nurse) "slaps" the unguarded skin hook into the surgeon's hand. Preferably, the surgeon should "feel" the orientation of the skin hook and automatically grip its handle without taking his (or her) eyes off of the patient or the instrumentation in the operating room. As a result, the nurse may accidentally or inadvertently be nicked by the exposed prong (or prongs) on the skin hook. Similarly, the surgeon risks being nicked when returning the skin hook to the nurse.

Being nicked by a skin hook can be extremely uncomfortable. In addition, and more importantly, it can lead to the spreading of infection and disease. Concern over this situation has become especially acute since the appearance and spreading of the HIV virus or "AIDS". There are similar concerns with the Hepatitis B virus (referred to as "HBV").

The risks associated with a nick or puncture from conventional unguarded skin hooks during an operating room procedure are greater than those associated with needle sticks; even there, however, the problem is becoming alarming. A study was made by the Needle Stick Surveillance Group of the C.D.C. (Centers for Disease Control). Out of 3,978 needle sticks from patients known to be HIV positive, 13 health care workers became infected—roughly 1 out of 300. Thus, from a single needle stick while treating an AIDS patient in an operating room or other environment, the chances are roughly 1 out of 300 that the surgeon, nurse or other individual health care provider will sero-convert and become HIV positive.

If a surgeon, nurse or assistant is nicked or stuck by a skin hook (rather than a needle stick) while conducting a surgical procedure, the risk is greater. This is simply because, first, there is more blood involved in a surgical procedure and, secondly, the surface area of the wound may be somewhat larger. In operating on an HIV positive patient, and even if the chances of becoming HIV positive from a puncture sustained from a skin hook are substantially the same as the needle sticks—roughly 1 out of 300 —if the surgeon or nurse gets stuck with a skin hook while performing just one operating room procedure on an HIV-positive patient per day for 6 days a week, 50 weeks per year, then the chances of becoming HIV positive through an inadvertent puncture from a skin hook in an operating room procedure are virtually guaranteed in just a one-year period.

This situation has become so pronounced that some leading surgeons (as well as nurses and other individual health care providers) have stopped performing surgical procedures or also have abandoned their respective practices altogether, rather than risk the chances of inadvertently contracting the deadly HIV virus from an infected patient.

While the use of protective gloves aid in reducing the chances of being nicked during a surgical procedure, the use of such gloves are by no means foolproof; and such nicks are still quite common. Even when two sets of gloves are utilized, full protection is not afforded to the health care provider, for many times the razor-sharp surgical prongs of the skin hook cut right through both sets of gloves. Also, utilizing two sets of gloves at the same time reduces the wearer's finger dexterity, thereby presenting problems with performing the intended surgical procedure and tending to reduce the effectivity thereof.

To prevent getting stuck by a skin hook, some surgeons have resorted to other instruments which are cumbersome and awkward to use (such as a large scissors). This is time consuming and inefficient.

As a result, some leading manufacturers in the field have reported declining sales of skin hooks over the past several years.

SUMMARY OF THE INVENTION

Accordingly, it is an object of the present invention to provide a guarded skin hook for selectively covering and uncovering the prong (or prongs) of the skin hook during a surgical procedure, thereby protecting against inadvertent contact and, especially, during transfer of the skin hook from the nurse to the surgeon (and vice versa) during the surgical. procedure.

It is another object of the present invention to provide a skin hook having a guard which may be advanced to cover the prong (or prongs) during transfer of the skin hook and which may be retracted to expose the prong (or prongs)—all in a one-handed operation or movement—without requiring the surgeon (or the nurse) to take his (or her) eyes away from the patient in order to visually observe the skin hook.

It is yet another object to provide a "slim line" guarded skin hook, without a cumbersome mechanism, so that the surgeon will have a comfortable "feel" of the instrument and be able to utilize a grip that substantially approximates the grip that is normally utilized on a conventional unguarded skin hook.

It is a further object to provide a guarded skin hook having a "solid" two-position detent mechanism between the guard and the handle of the skin hook, so that the guard will not inadvertently slip; and wherein the detent mechanism may be released easily and with an auditory "click", so that the user is made aware that the guard has been locked into its desired position and, again, in a one-handed movement and without having to remove his (or her) eyes away from the patient or the instrumentation in the operating room.

In accordance with the teachings of the present invention, a preferred embodiment of a guarded skin hook is herein disclosed and claimed. This guarded skin hook includes a handle having a shank terminating in at least one downwardly-depending rearwardly-projecting prong or hook formed thereon. The handle further includes a pair of longitudinal guide tracks formed therein, and a guard has a pair of inturned laterally-extending flanges slidably received in the respective guide tracks on the handle. As a result, the guard has an advanced position in which the hook is guarded and further has a retracted position in which the hook is exposed. A manually-releasable detent means is provided between the guard and the handle, and means are further provided for limiting the longitudinal sliding movement of the guard on the handle. The guard has a forwardly-extending downwardly-offset portion substantially covering the hook in the advanced position of the guard, thereby precluding inadvertent contact with the hook.

The forwardly-extending downwardly-offset portion of the guard includes a substantially-flat section which is disposed below the hook, extends laterally thereof, and terminates in respective side edges. The distances between the sharp point of the hook (or hooks) and the respective elements of the guard are within min/max ranges, respectively, thereby precluding inadvertent contact with the hook.

In this preferred embodiment, the handle is substantially flat, the top portion of the handle is provided with transverse ridges, and the detent means includes a detent button extending downwardly from the handle. With this structural arrangement, a health care provider (receiving the guarded skin hook) will know intuitively whether the guard is advanced or retracted—as well as the orientation of the guarded skin hook ("up" or "down")—without being required to visually examine the guarded skin hook.

Viewed in another aspect, the present invention provides an improved method of using a surgical instrument following an incision on a patient, wherein the instrument has at least one hook thereon, and wherein a guard is carried by the instrument, the guard having a retracted position in which the hook is exposed and further having an advanced position in which the hook is substantially covered against inadvertent or accidental contact. The improved method includes the steps of retracting the guard to expose the hook, inserting the hook of the instrument into the incision on the patient, moving the guard back towards the hook, such that the skin is substantially clamped between the hook and the guard and does not slip off the hook, and moving the instrument away from the incision to peel away the skin from the incision. Preferably, the instrument comprises a skin hook.

This prevents the O.R. personnel from poking themselves when feeling for the thickness of the skin flap, as well as guarding the O.R. personnel should the hook become released from the flap.

These and other objects of the present invention will become readily apparent from a reading of the following description of the present invention, taken in conjunction with the enclosed drawings.

BRIEF DESCRIPTION OF THE DRAWINGS

FIG. 3 is a side elevation of a first embodiment of the guarded skin hook of the present invention, showing the shank of the skin hook extended beyond the guard to expose the prong (or prongs) for use during the surgical procedure.

FIG. 4 is a rear end view of the guarded skin hook of FIG. 3, drawn to an enlarged scale.

FIG. 5 is a front view, drawn to an enlarged scale, showing the shank of the skin hook retracted within the guard to cover the prong (or prongs) of the skin hook during transfer of the skin hook from the nurse to the surgeon (and vice versa) in the operating room.

FIG. 6 is a side elevation of the guarded skin hook of FIG. 5, corresponding substantially to FIG. 3, but showing the shank retracted within the guard.

FIG. 7 is a longitudinal sectional view taken along lines 7—7 of FIG. 4, showing the prongs in their extended position and, conversely, the guard in its retracted position.

FIG. 8 is a longitudinal sectional view taken along lines 8—8 of FIG. 5, corresponding to FIG. 7, but showing the prongs in their retracted position and, conversely, the guard in its advanced position.

FIG. 11 is a cross-sectional view taken along lines 11—11 of FIG. 8, drawn to an enlarged scale, and showing the guard slidably mounted on the main body of the skin hook.

FIG. 12 corresponds substantially to FIG. 11, but shows a modification thereof, wherein the guard and the main body of the skin hook are complementary-shaped (preferably hexagonal) so as to be keyed to one another, thereby preventing relative rotation therebetween.

FIG. 15 illustrates how the guard protects the assistant's hand when the guarded skin hook is passed from the assistant to the surgeon during an operating procedure.

FIG. 16 illustrates how the prong (or prongs) are advanced and, conversely, the guard is retracted to expose the prong (or prongs) for normal use of the instrument, wherein the movement is one-handed and without looking at the instrument.

FIG. 17 illustrates how the prong (or prongs) are retracted and, conversely, the guard is advanced to again cover the prong (or prongs) for transferring the instrument in the O.R. and, again, in a one-handed movement without looking at the instrument.

FIG. 18 illustrates how the guard protects the surgeon's hand when the guarded skin hook is passed from the surgeon back to the assistant during an operating procedure.

FIG. 19 is a perspective view of an alternate (and preferred) embodiment of the present invention, showing the skin hook in its unguarded position.

FIG. 20 is a further perspective view, corresponding substantially to FIG. 19, but showing the skin hook in its guarded position.

FIG. 21 is a side elevational view of the guarded skin hook of FIG. 19, showing the guard retracted on the handle.

FIG. 22 is a side elevational view of the guarded skin hook of FIG. 20, showing the guard advanced on the handle.

FIG. 23 is a top plan view thereof, drawn to an enlarged scale, and showing the guard in its advanced (or closed) position.

FIG. 24 is a bottom plan view thereof, drawn to an enlarged scale.

FIG. 25 is a cross-sectional view thereof, taken along the lines 25—25 of FIG. 23 and drawn to an enlarged scale, showing the guide tracks in the handle for receiving the lateral inturned flanges on the guard, and further showing the two-position detent mechanism between the guard and the handle.

FIG. 26 is a longitudinal cross-sectional view, taken along the lines 26—26 of FIG. 23 and drawn to an enlarged scale, and showing a stop pin carried by the handle and received in a closed longitudinal slot formed in the guard, thereby limiting the degree of longitudinal movement of the guard on the handle.

FIG. 27 is a pictorial view of the forward portion of FIG. 19, drawn to an enlarged scale, and showing how the guard in its closed position to prevent inadvertent contact with the prongs (or hooks).

FIG. 28 corresponds substantially to FIG. 27, but shows an alternate structure for the guard so as to provide additional protection.

FIG. 29 is a further pictorial view, showing a concave substantially spoon-shaped guard.

FIG. 36 shows the conventional unguarded skin hook inserted into an incision made on the patient. FIG. 37 shows the patient's skin being lifted away from the incision by the conventional unguarded skin hook. FIG. 38 shows the patient's skin falling off the conventional unguarded skin hook.

FIGS. 39–41 schematically illustrate the additional feature and advantage of the improved guarded skin hook of the present invention. More specifically, FIG. 39 shows the guarded skin hook being inserted into the incision, the guard being retracted. FIG. 40 shows the guard being advanced to clamp the patient's skin between the hook (or hooks) and the guard. FIG. 41 shows the clamped skin being pulled away from the incision and precluded from falling off of the hook (or hooks).

DESCRIPTION OF THE PREFERRED EMBODIMENTS

Figure 1:
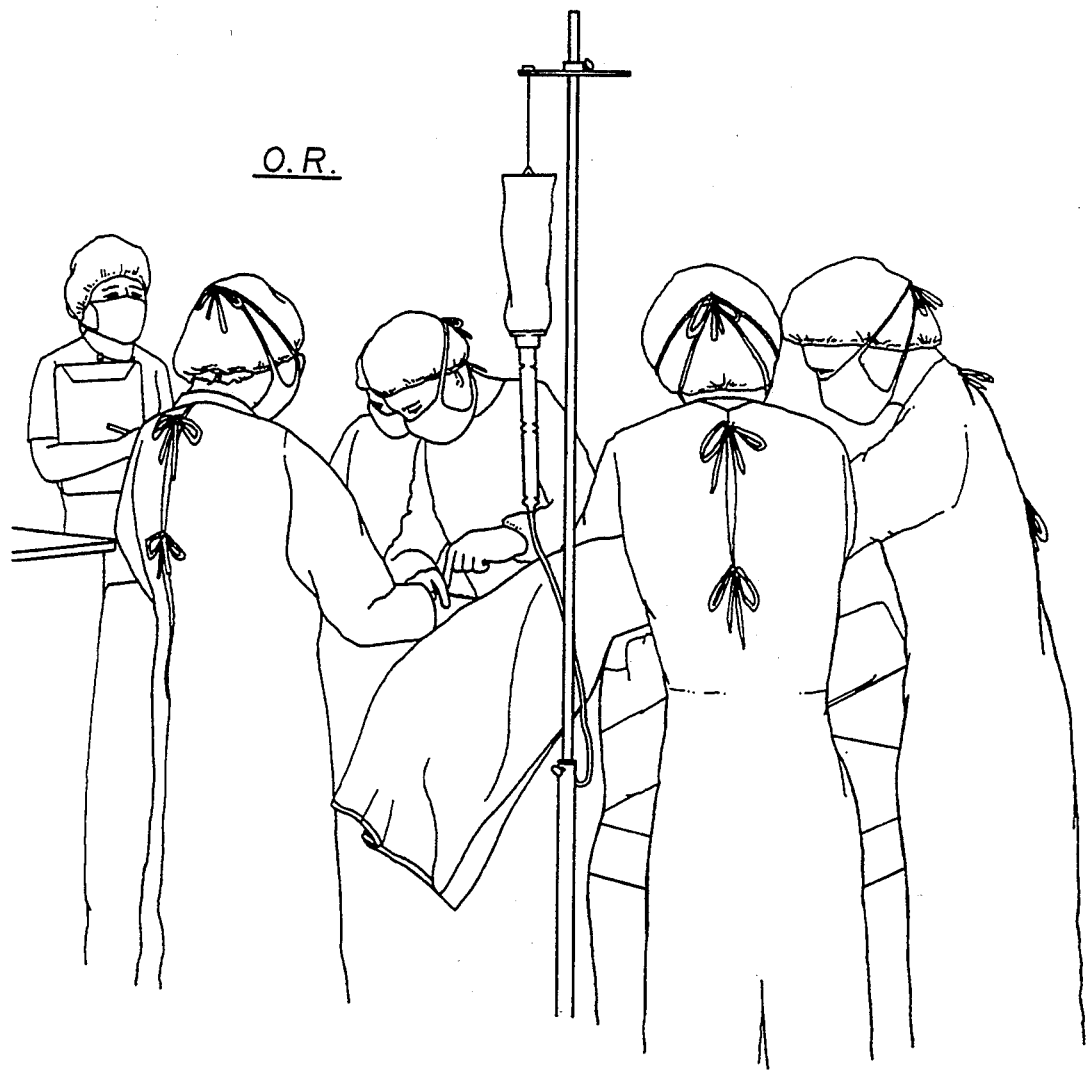
FIG. 1 is a perspective view of an operating room in a hospital or clinic, where the guarded skin hook of the present invention will be utilized.

With reference to FIG. 1, the situation in an operating room ("O.R.") is tense and dynamic, seconds often count, and mistakes can mean the difference between life or death for the patient. Anything which distracts the lead surgeon (as well as the assistants, nurses, O.R. technicians or other health care providers) is counterproductive. If the patient is known to be H.I.V.-infected or a known carrier of hepatitis, an additional (and considerable) stress is placed on the O.R. personnel.

Figure 2A:
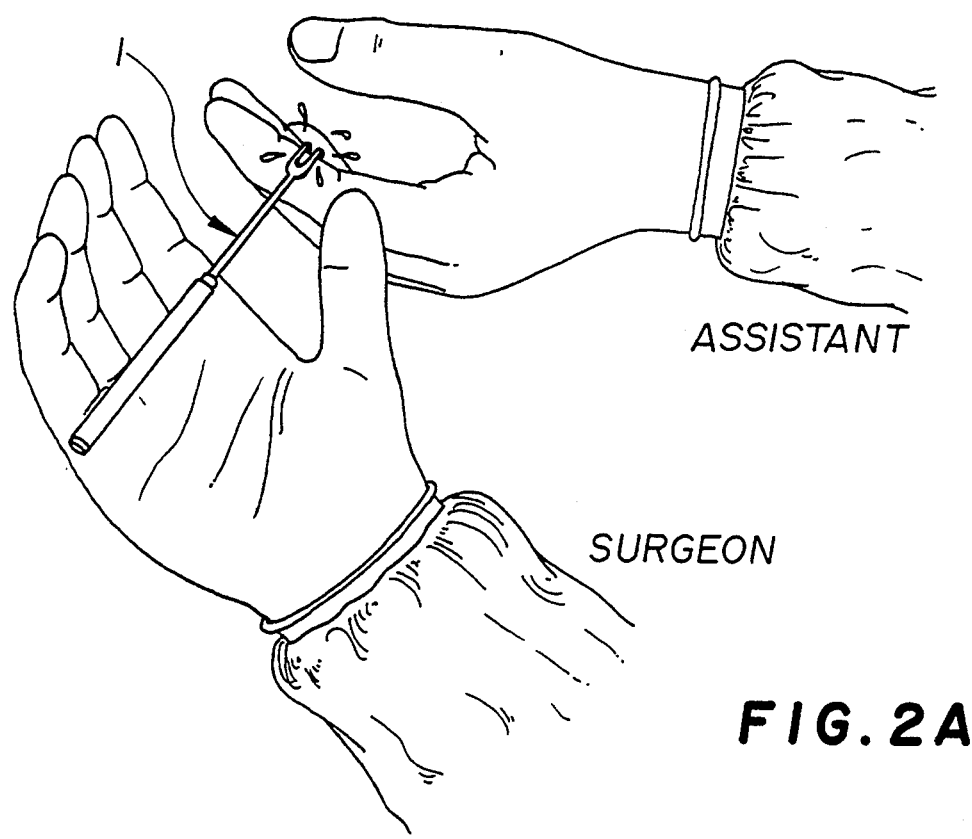
FIG. 2A is an enlarged view of a conventional skin hook, illustrating the problems that can occur to an assistant when passing a conventional skin hook to a surgeon during an operating procedure.
Figure 2B:
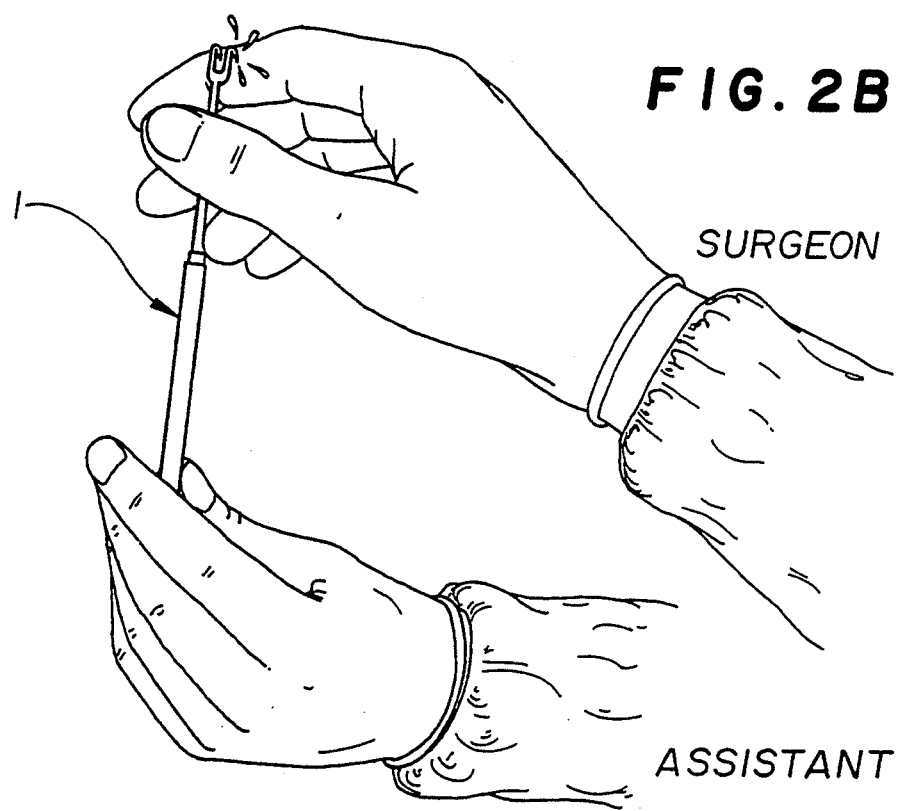
FIG. 2B is an enlarged view of a conventional skin hook, illustrating the problems that can occur to a surgeon when passing a conventional skin hook back to the assistant during an operating procedure.

In transferring a conventional unguarded skin hook from the nurse (or other assistant) to the surgeon, as shown in FIG. 2A, the nurse is occasionally nicked or cut by the prongs or hooks on the skin hook. Conversely, as shown in FIG. 2B, the surgeon may be nicked or cut when transferring the conventional unguarded skin hook back to the nurse.

Figure 13:
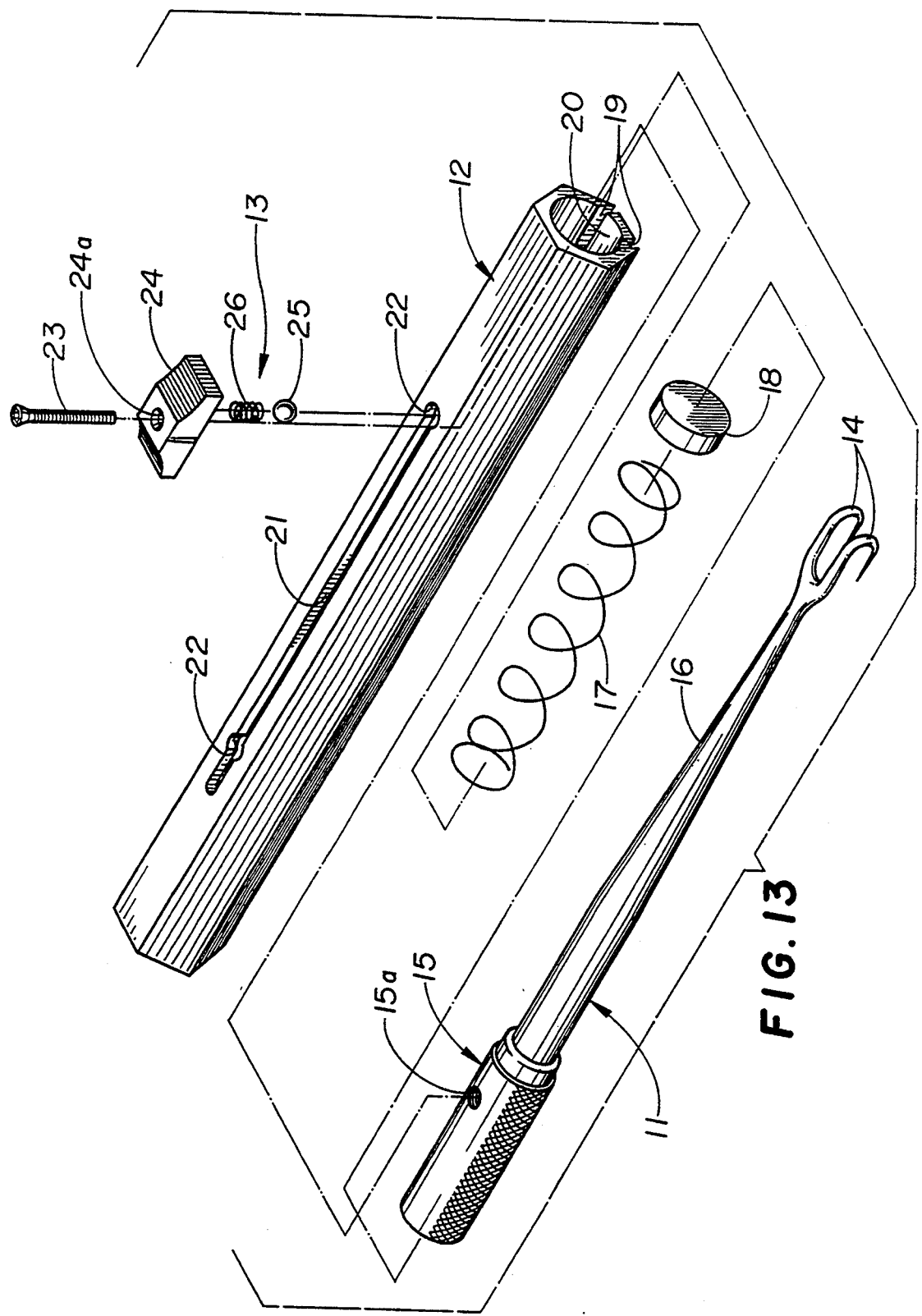
FIG. 13 is an exploded perspective view of the guarded skin hook of the present invention.

With reference to FIGS. 3–13, the guarded skin hook 10 of the present invention includes a skin hook 11 slidably received within a guard 12 and releasably retained therein by a twoposition detent mechanism 13. The skin hook 11 includes a main body portion 15, a shank 16 extending forwardly therefrom, and at least one prong or hook 14 formed on the shank 16 and extending downwardly and rearwardly therefrom. In this embodiment, the guard 12 is formed as a sleeve, and the shank 16 is constantly urged out of the guard 12 by a spring 17 (or other resilient means) disposed within the guard 12 and lodged between the closed rear end 12a of the guard 12 and a disc 18 rearwardly of the main body portion 15 of the skin hook 11. When the skin hook 11 is fully retracted within the guard 12, as shown in FIG. 8, the hook (or hooks) 14 are received within slots 19 formed in the forward portion 20 of the guard 12, as shown in FIG. 13.

The detent mechanism 13 includes a longitudinal slot 21 preferably formed on top of the guard 12, and this slot 21 terminates in respective detent pockets 22 at each end thereof. A screw 23 passes through a hole 24a in a manually-actuated detent button 24, through the slot 21, and is received in a tapped recess 15a in the main body portion 15 of the skin hook 11, thereby securing the main body portion 15 to the detent button 24. This detent button 24 has a blind bore 24b, forwardly of the screw 23 and parallel thereto as shown more clearly in FIG. 9, and a spring 26 is seated in this blind bore and constantly urges a detent ball 25 outwardly therefrom. The detent ball 25 rides in the slot 21, as the guard 12 is actuated, and is received in one (or the other) of the detent pockets 22.

Figure 14:
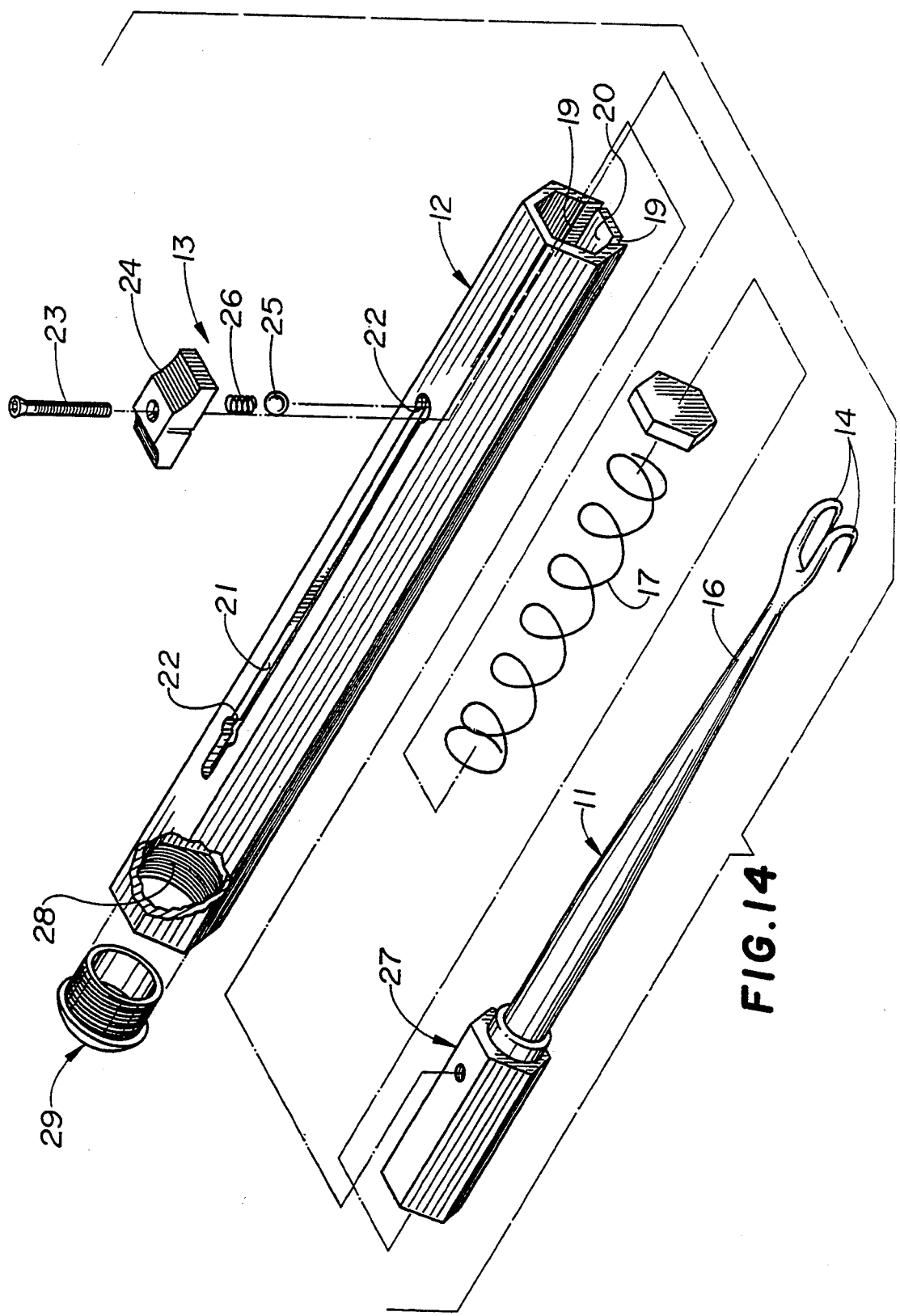
FIG. 14 is another exploded perspective view, corresponding substantially to FIG. 13, but showing an alternate construction of the guarded skin hook of the present invention.
Figure 15:
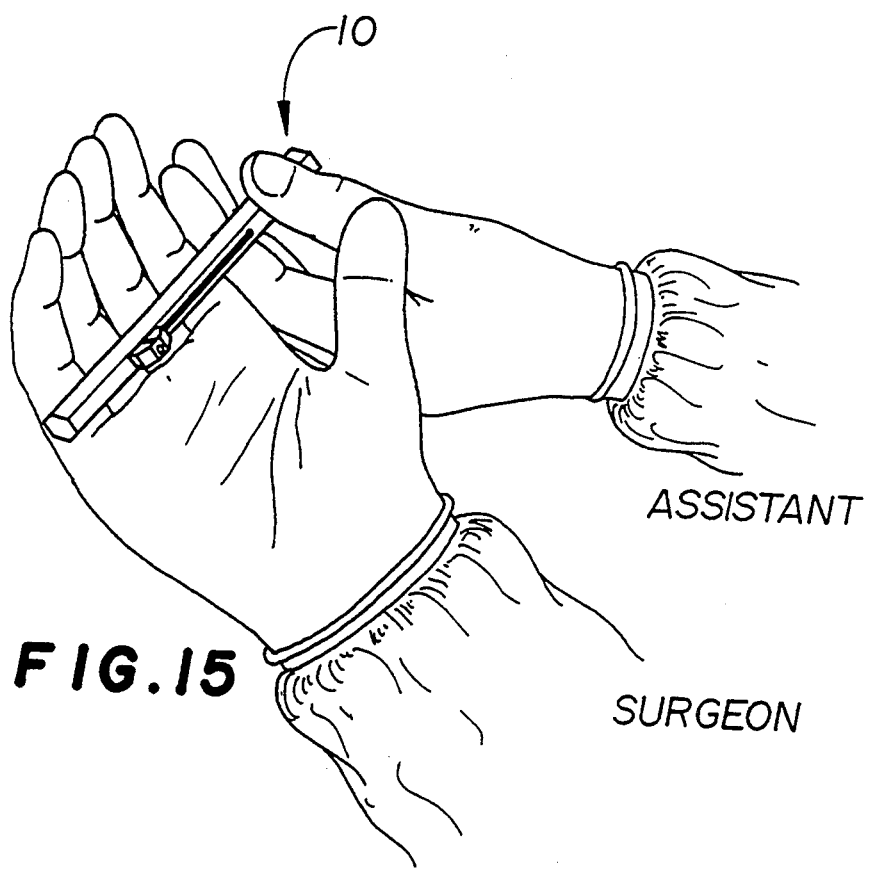
FIGS. 15–18 are pictorial views illustrating the use of the guarded skin hook of FIGS. 3–13 and, in particular, the protection afforded to the health care providers in passing or transferring the guarded skin hook during an operating procedure.
Figure 16:
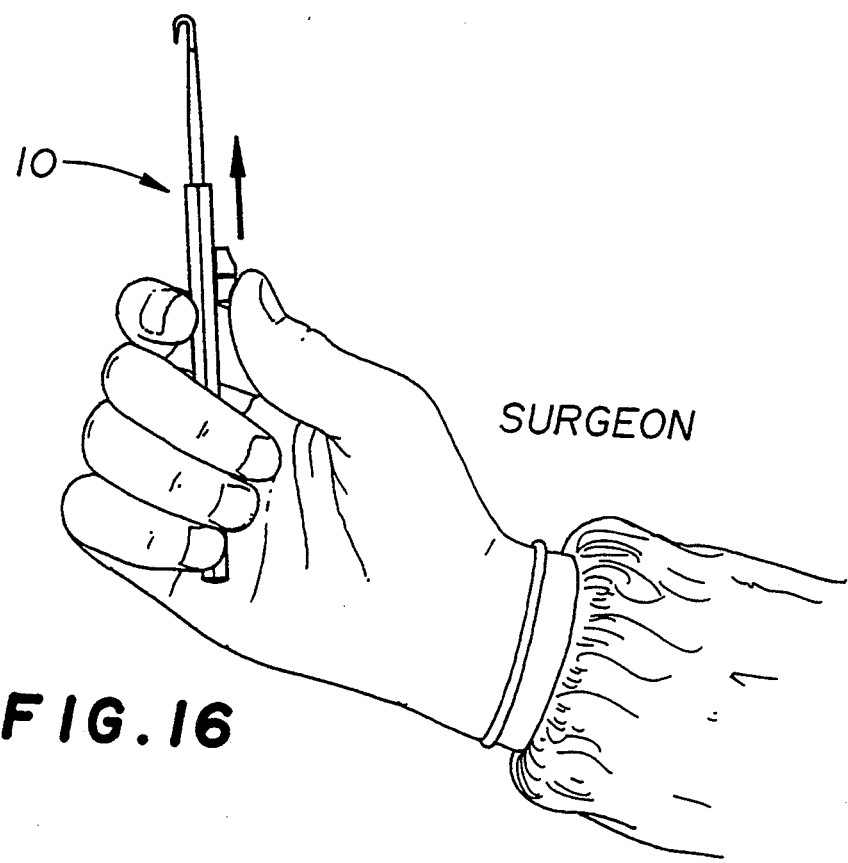
Figure 17:
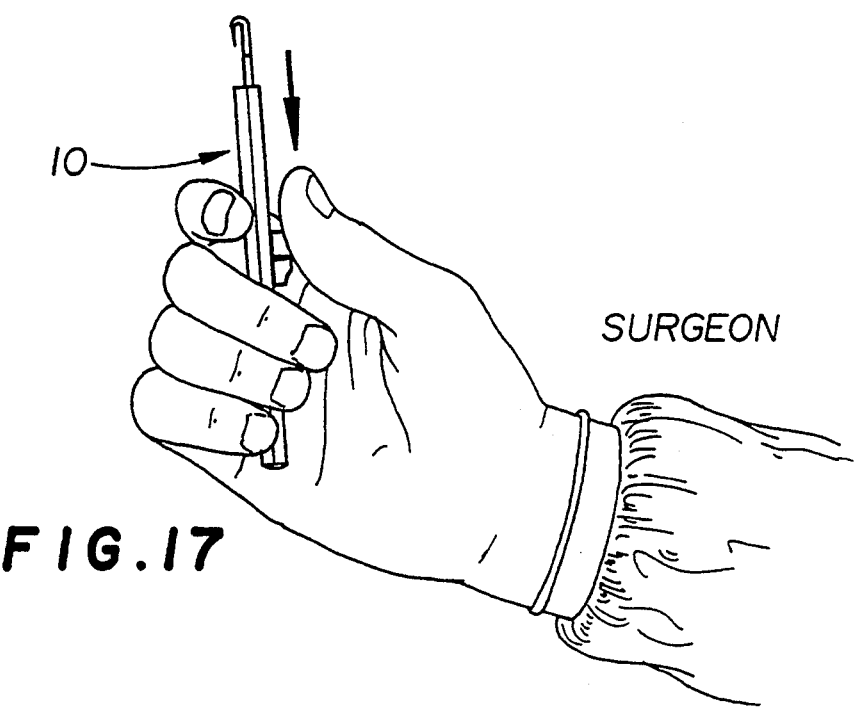
Figure 18:
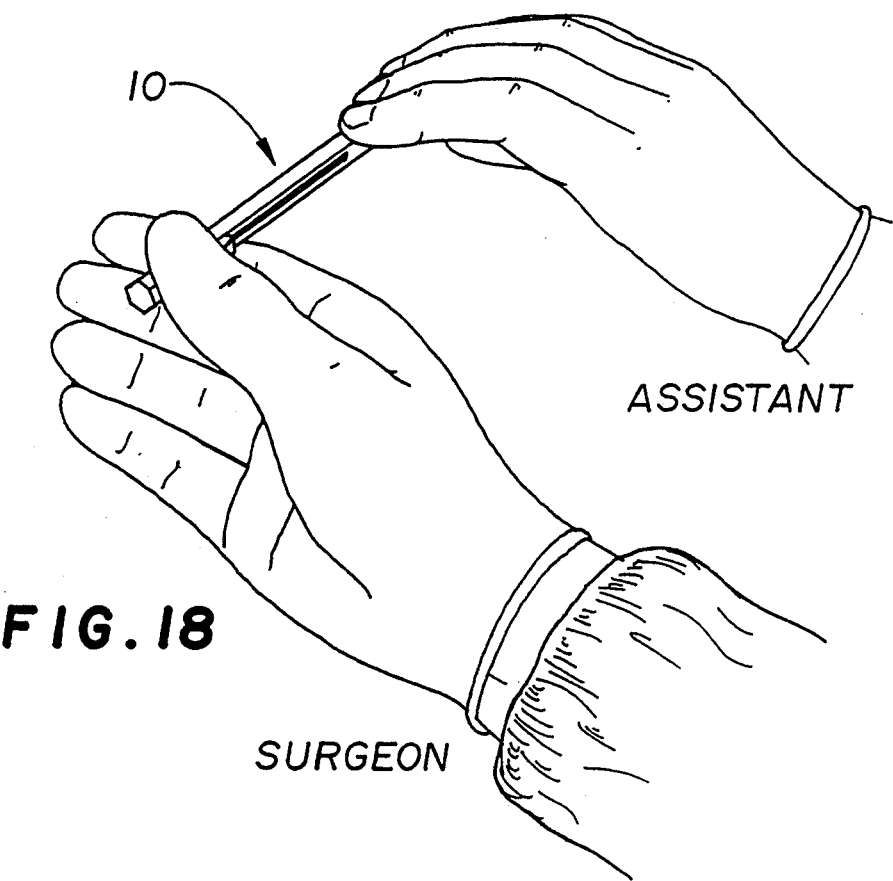

With reference to the alternate construction of FIGS. 12 and 14, the main body portion 27 is hexagonal and is keyed to the hexagonal sleeve constituting the guard 12, thereby preventing relative rotation therebetween. The rear end portion of the guard 12 is open and has internal threads 28 cooperating with an externally-threaded cap 29, thereby facilitating assembly of the guarded skin hook 10.

Figure 10:
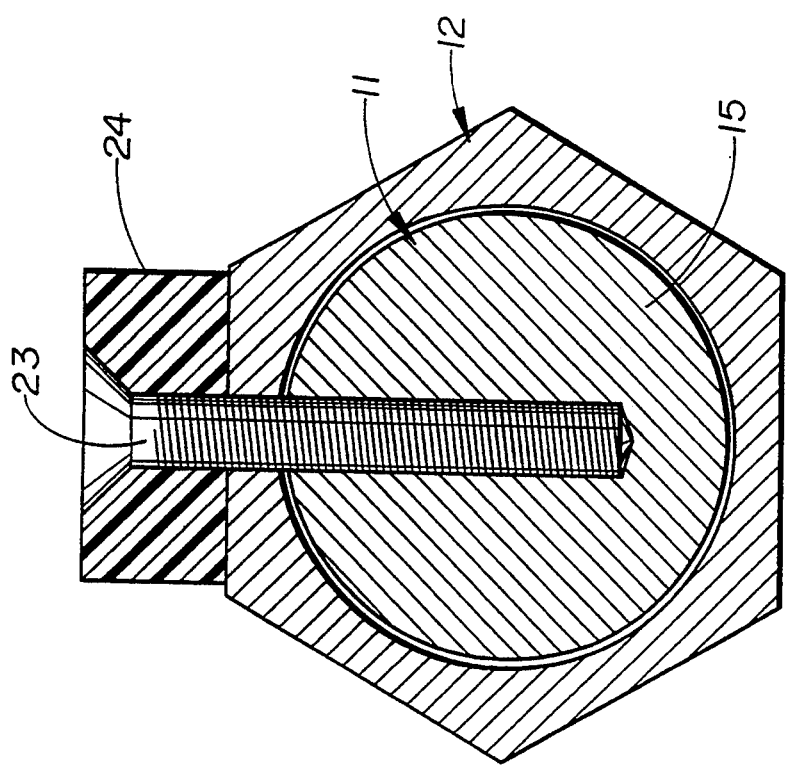
FIG. 10 is a cross-sectional view taken along lines 10—10 of FIG. 8, drawn to an enlarged scale, and showing the button for manually activating the shank relative to the guard (and against the retention of the detent mechanism).
Figure 9:
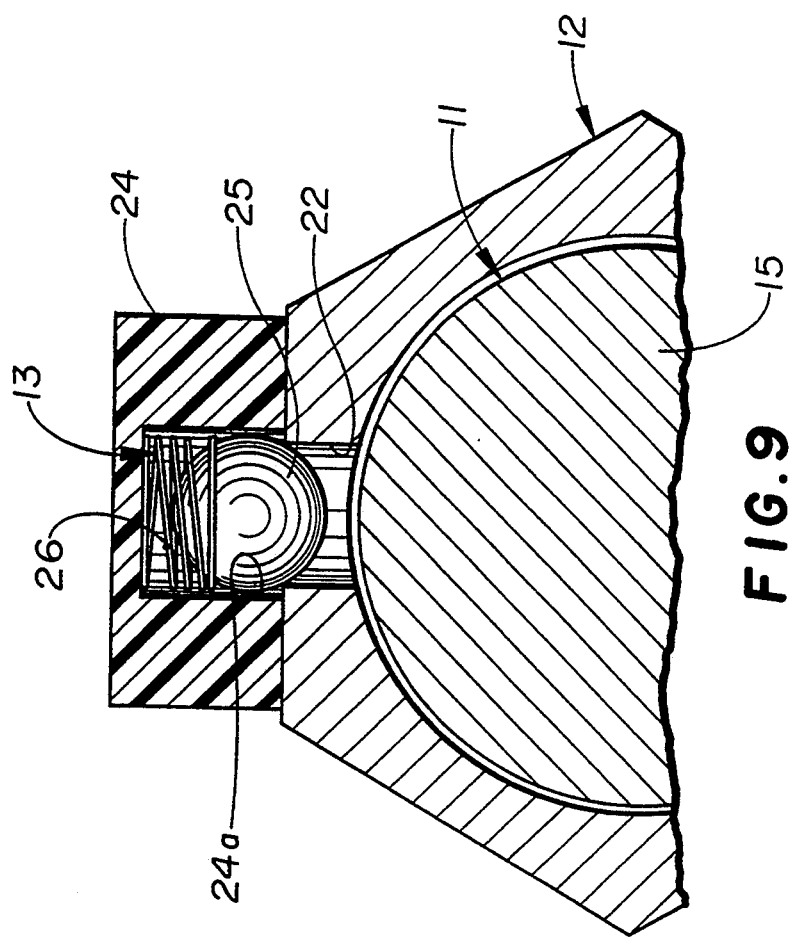
FIG. 9 is a cross-sectional view taken along lines 9—9 of FIG. 8, drawn to an enlarged scale, and showing the detent mechanism.

With reference to FIGS. 15–18, the guarded skin hook 10 (in its closed, guarded position) may be passed freely from the assistant to the surgeon (FIG. 15) and the surgeon may release the skin hook 11 (conversely, retracting the guard 12) to expose the hook (or hooks) or prong (or prongs) 14 for use during the operating procedure (FIG. 10). Thereafter, the skin hook 11 may be retracted (and, conversely, the guard advanced) as shown more clearly in FIG. 17, to cover the hook or hooks 14. Thereafter, the guarded skin hook 10 may be passed freely back to the assistant in the O.R. (FIG. 18) and, again, while protecting against inadvertent or accidental nicks or cuts.

With reference to FIGS. 19–26, there is illustrated a preferred embodiment 100 of the guarded skin hook of the present invention. The guarded skin hook 100 includes a handle 101, which preferably is substantially flat, and is secured to a shank 102 extending forwardly therefrom. The shank 102, in turn, is provided with at least one prong or hook 103 bent downwardly and rearwardly thereof.

A pair of longitudinal guide tracks 104 is formed in the respective sides of the handle 101, and a guard 105 has a pair of respective inturned lateral flanges 106 received in the guide tracks 104 (as shown more clearly in FIG. 25) thereby slidably mounting the guard 105 (FIG. 26) on the handle 101. A pin 107 is carried by the handle 101, transversely thereof, and is received in a closed longitudinal slot 108 formed in the guard 105 (FIG. 26) thereby limiting the longitudinal sliding movement of the guard 105 on the handle 101. As a result, the guard 105 has an advanced position (relative to the handle 101) in which the hook 103 is covered and, conversely, a retracted position in which the hook 103 is exposed.

A two-position manually-releasable detent mechanism 109 is provided between the guard 105 and the handle 101, thereby providing a "solid" detented connection between the guard 105 and the handle 101 and preventing inadvertent or accidental movement of the guard 105. This detent mechanism 109 includes a detent button 110 carried by the guard 105 and depending downwardly therefrom. The detent button 110 has a blind bore 111 provided with a spring 112 for constantly urging a detent ball 113 outwardly of the bore 111. This detent ball 113 is received, alternately, in a pair of detent pockets 114 and 115, respectively, formed in the bottom surface 116 of the handle 101. Preferably, the bottom surface 116 has a longitudinal groove 117 formed thereon between the detent pockets 114 and 115, respectively, thereby facilitating movement of the detent ball 113 carried by the detent button 110.

With further reference to FIGS. 27–29, preferably the guard 105 is substantially flat and has a forwardly-extending downwardly-offset portion 118, including a depending section 119 and a forward section 120, each of which is substantially flat. The forward section 120 extends below the hook (or hooks) 103 and has side edges 121 which extend laterally beyond the lateral extent of the hook (or hooks) 103, as shown more clearly in FIGS. 23 and 27.

In FIG. 28, the forward section 120 is provided with diagonally-cut vertical flanges 122, thereby providing additional protection against inadvertent or accidental contact with the hooks 103.

In FIG. 29, the guard 105 has a forwardly-extending substantially spoon-shaped concave portion 123 disposed below the hook or hooks 103 and having respective curved sections 124 extending upwardly and laterally of the hook or hooks 103.

Figure 30:
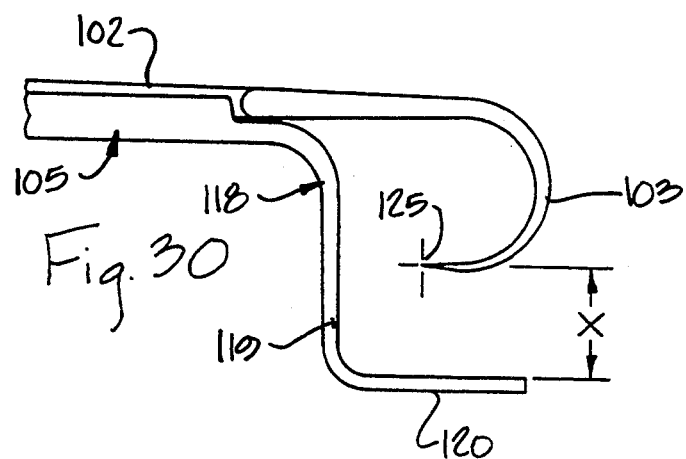
FIGS. 30–32 illustrate, schematically, the dimensional considerations of the forwardmost offset portion of the guard and the sharp point on the hook (or hooks).
Figure 31:
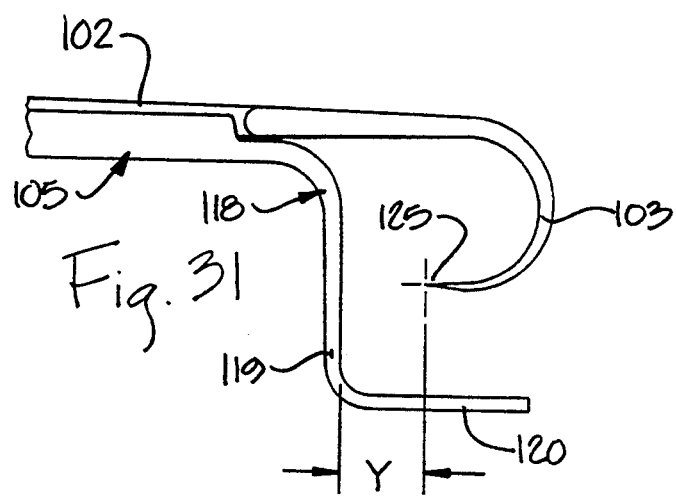
Figure 32:
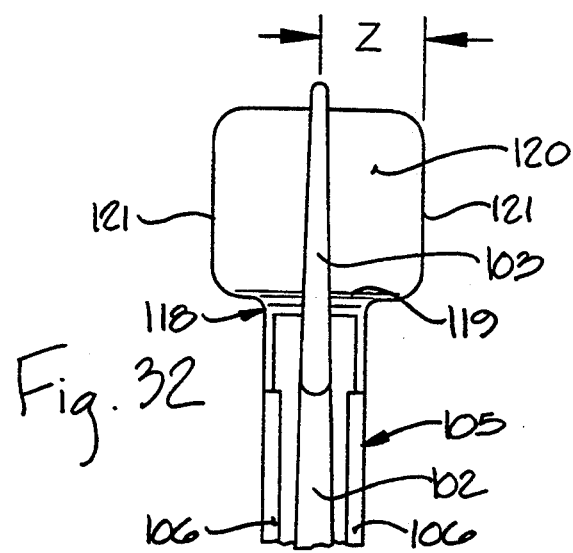

With reference to FIGS. 30–32, the distance between the sharp point 125 of the hook or hooks 103 and the top of the flat (lower) forward section 120 is denoted by X; between the sharp point 125 and the front of the flat depending section 119 by Y; and between the sharp point 125 and the lateral side edge (or edges) 121 of the flat (lower) forward section 120 by Z. In an operating model of the preferred embodiment, the guarded skin hook is approximately seven inches long, and the min/max ranges for these dimensions are as follows:

X=2 to 10 mm.
Y=2 to 10 mm.
Z=2 to 10 mm.

On this particular instrument, these ranges are intended to provide a minimum opening or "window" to the sharp point 125 of the hook or hooks 103 of sufficient size to prevent the insertion of a finger tip, yet not obscure the surgeon's vision of the sharp point 125.

Figures 33, 34, 35:
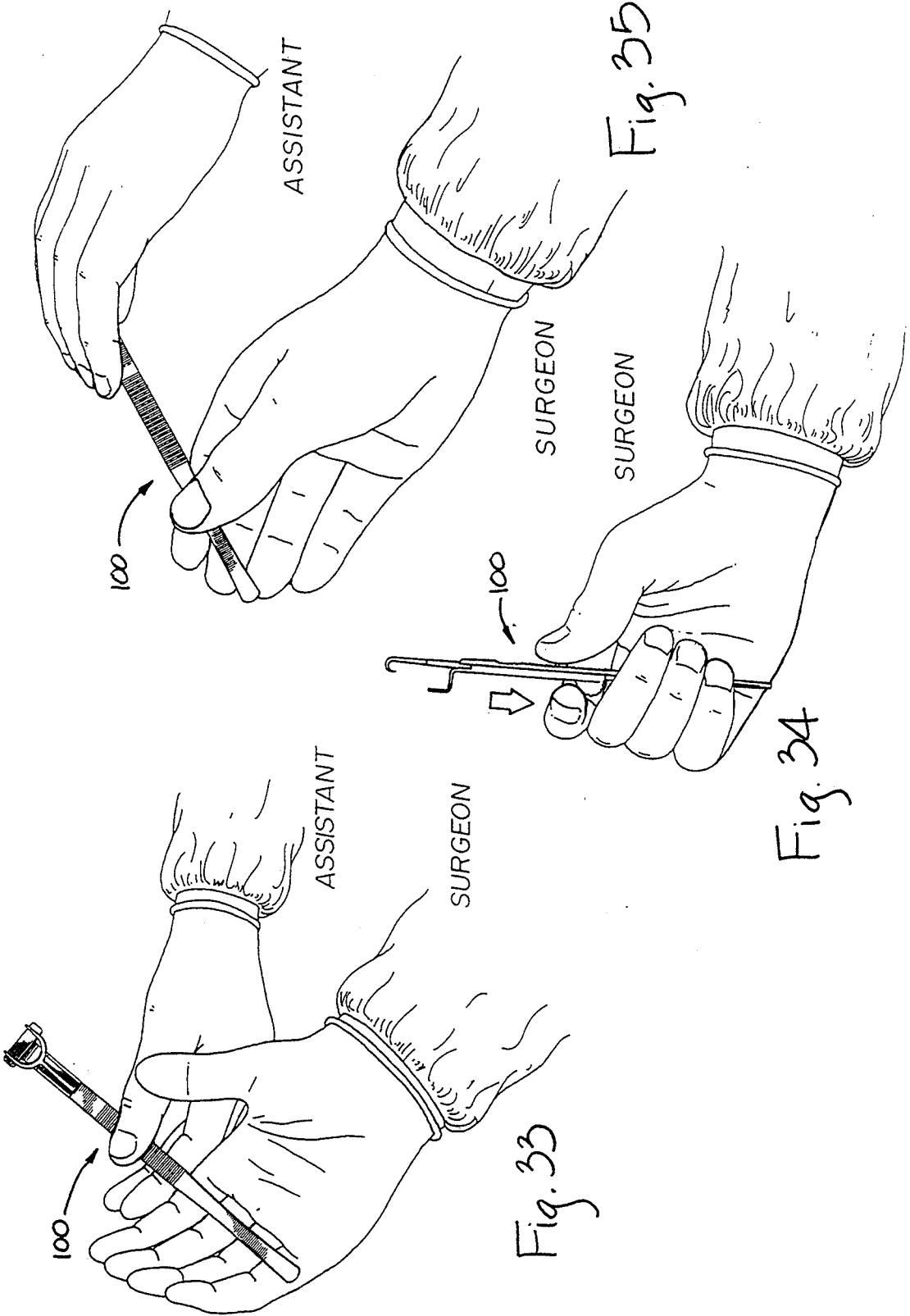
FIG. 33 is a pictorial view, showing the nurse transferring the guarded skin hook to the surgeon during an operating procedure, such that the surgeon does not have to take his (or her) eyes off of the patient or the instruments in the operating room.
FIG. 34 is a further pictorial view, corresponding to FIG. 33, but showing how the surgeon may retract the guard—using only one hand—and without looking at the guarded skin hook.
FIG. 35 is a still further pictorial view, showing the surgeon advancing the guard on the handle and transferring the guarded skin hook back to the nurse (or other assistant) in the operating room.

With reference to FIGS. 33–35, the nurse may transfer the guarded skin hook 100 to the surgeon with the guard 105 in its advanced (or closed) position (FIG. 33), thereby preventing the nurse from being nicked or cut. The top of the handle 101 has transverse ridge 126 together with a concave recess 126A while the detent button 110 has serrations 127. In using the guarded skin hook 100, the surgeon's thumb may be in the concave recess 126A and his (or her) forefinger on the serrated detent button 110. Accordingly, the surgeon will know intuitively from the tactile "feel" of the guarded skin hook 100, first, whether the guard 105 is "on" (that is, in its advanced or closed position) and, secondly, the relative orientation of the instrument (that is, whether the guarded skin hook 100 is "up" or "down") as shown in FIG. 34. The same situation prevails when the surgeon passes the guarded skin hook 100 back to the nurse (FIG. 35).

In each case, the guarded skin hook 100 may be passed back and forth in the O.R.—safely and without risking a potentially-dangerous nick or cut—and the guard 105 may be activated with one hand without requiring the recipient, such as the surgeon, to take his (or her) eyes off of the patient or the instrumentation in the O.R. Additionally, the detent mechanism 109 provides an auditory "click", so that the recipient will know that the guard 105 has been moved into its selected alternate position.

As will be appreciated by those skilled in the art, the teachings of the present invention are equally applicable to other medical instruments (other than a skin hook) including a surgical pick, a dental scaler and a periodontal scaler.

The guarded skin hook 100 has another, and very valuable, feature and advantage.

Figure 36:
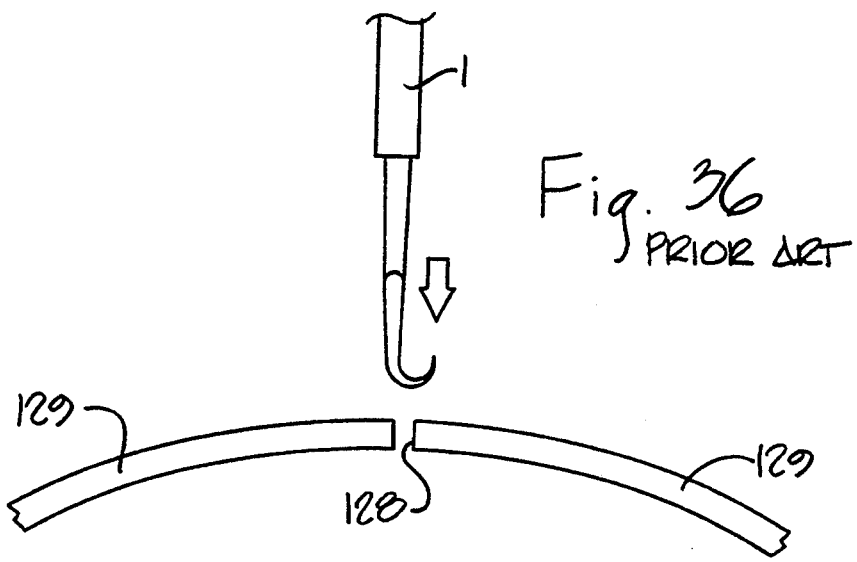
FIG. 36–38 schematically illustrate the problems incurred during use of a conventional unguarded skin hook heretofore resorted to in the prior art. More specifically.
Figure 37:
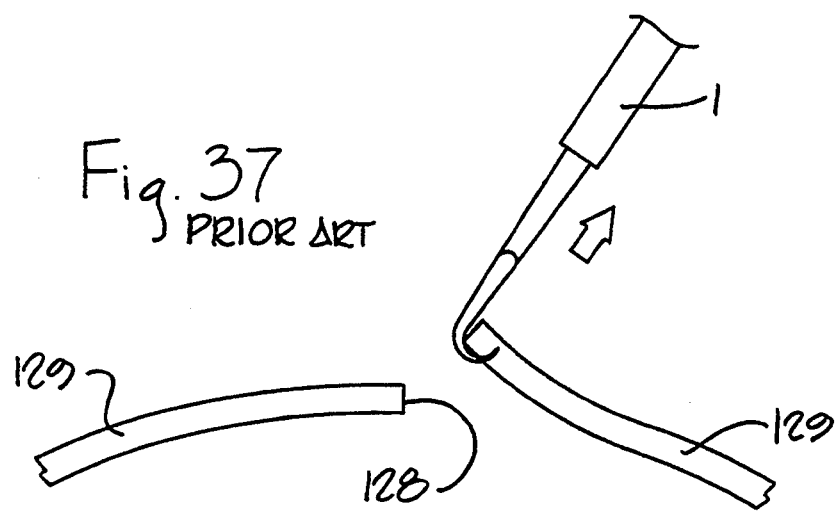
Figure 38:
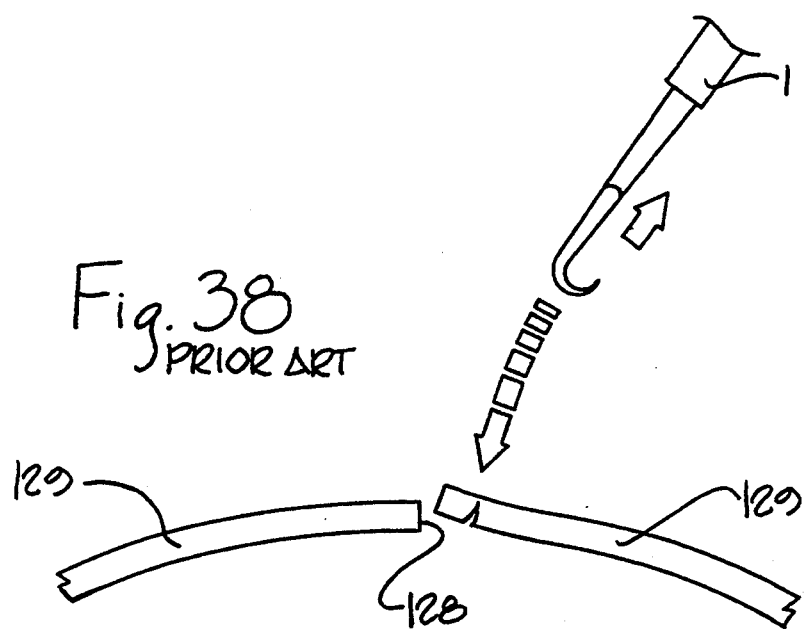

With the conventional unguarded skin hooks, used widely in the prior art, there is an inherent problem in that the patient's skin (that is being peeled back from an incision) often falls off of the hook. This problem is illustrated schematically in FIGS. 36–38. In FIG. 36, the hook 103 (of a conventional unguarded skin hook 1) is inserted into an incision 128 previously made in the patient. In FIG. 37, the hook 103 engages the patient's skin 129 and lifts or peels the skin 129 away from the incision 128. In some cases, such as ear, nose and throat ("ENT") surgery, or plastic surgery, the skin hook will be left "dangling" (not shown) and the weight of the skin hook keeps the skin 129 peeled away from the incision 128. However, the skin 129 often slips off of the hook 103, as shown in FIG. 38, and this disrupts the surgical procedure and is at least distracting, if not somewhat dangerous.

This problem of long-standing is corrected by the method employed in using the guarded skin hook 100 of the present invention, as shown in FIGS. 39–41.

In FIG. 39, the hook 103 of the guarded skin hook 100 is inserted into the incision 128 to begin lifting the skin 129, similarly to FIG. 36. However, the guard 105 is then advanced forwardly (FIG. 40) to firmly clamp the skin 129 between the guard 105 and the hook (or hooks) 103. Thereafter, and as shown in FIG. 41, the skin 129 may be lifted away from the incision 128 without the skin 129 slipping off of the hook 103.

Obviously, many modifications may be made without departing from the basic spirit of the present invention. For example, the present invention is applicable to all sizes of relevant instruments, such as large bone hooks used in orthopedics, as well as skin hooks and bone hooks used in veterinary medicine. Accordingly, it will be appreciated by those skilled in the art that within the scope of the appended claims, the invention may be practiced other than has been specifically described herein.

What is claimed is:

1. A guarded skin hook, comprising a handle including a shank having at least one downwardly-extending hook formed thereon, the handle further including a pair of longitudinal guide tracks formed thereon, a guard having a pair of inturned laterally-extending flanges slidably received in the respective guide tracks, such that the guard has a longitudinal sliding movement on the handle, and such that the guard has an advanced position in which the hook is guarded and further has a retracted position in which the hook is exposed, manually-releasable detent means between the guard and the handle, means for limiting the longitudinal sliding movement of the guard on the handle, and the guard having a forwardly-extending downwardly-offset portion substantially guarding the hook in the advanced position of the guard, thereby precluding inadvertent contact with the hook.

2. The guarded skin hook of claim 1, wherein the handle is substantially flat, wherein the handle has a top portion provided with transverse ridges, and wherein the detent means includes a detent button extending downwardly from the guard, such that a health care provider receiving the guarded skin hook will know intuitively whether the guard is advanced or retracted, as well as the orientation of the guarded skin hook, without being required to visually examine the guarded skin hook.

3. A guarded skin hook for use during a surgical procedure, comprising a handle including a shank having a longitudinal axis and further having a pair of parallel downwardly-projecting rearwardly-extending hooks formed thereon, one on each side of the longitudinal axis of the shank, a guard and means for slidably mounting the guard on the handle for relative limited longitudinal movement therebetween, two-position spring-loaded detent means between the guard and the handle, such that the guard has a retracted position in which the hooks are exposed for use during the surgical procedure, and such that the guard further has an advanced position in which the hooks are substantially guarded, the guard including a forward portion which is disposed below the hooks in the advanced position of the guard, and the forward portion of the guard having respective portions extending laterally beyond the hooks, respectively, thereby preventing accidental or inadvertent contact with the hooks in transferring the guarded skin hook from one health care provider to another during the surgical procedure.

4. A guarded skin hook for use during a surgical procedure, comprising a handle including a shank having at least one downwardly-projecting rearwardly-extending hook formed thereon, a guard and means for slidably mounting the guard on the handle for relative limited longitudinal movement thereon, the guard having a retracted position in which the hook is exposed for use during the surgical procedure, and the guard further having an advanced position in which the hook is substantially guarded, the guard including a forward portion which is disposed below the hook in the advanced position of the guard, and the forward portion of the guard having respective portions extending laterally beyond the hook, thereby preventing accidental or inadvertent contact with the hook in transferring the guarded skin hook from one health care provider to another during the surgical procedure, wherein the means to slidably mount the guard on the handle comprises, in combination, the guard having a pair of parallel sides, each of which is provided with an inturned flange, and the handle having a pair of guide tracks formed therein and receiving the respective inturned flanges on the guard.

5. The guarded skin hook of claim 3, wherein the guard has a longitudinal sliding movement on the handle, further including a pin carried by the handle transversely thereof, and the guard having a closed longitudinal slot formed therein and receiving the pin, thereby providing a stop means for limiting the longitudinal sliding movement of the guard on the handle, the stop means being independent of the detent means.

6. A guarded skin hook for use during a surgical procedure, comprising a handle including a shank having at least one downwardly-projecting rearwardly-extending hook formed thereon, a guard and means for slidably mounting the guard on the handle for relative limited longitudinal movement thereon, the guard having a retracted position in which the hook is exposed for use during the surgical procedure, and the guard further having an advanced position in which the hook is substantially guarded, the guard including a forward portion which is disposed below the hook in the advanced position of the guard, and the forward portion of the guard having respective portions extending laterally beyond the hook, thereby preventing accidental or inadvertent contact with the hook in transferring the guarded skin hook from one health care provider to another during the surgical procedure, wherein the guard has a blind transverse bore formed therein, a detent ball in the bore, a spring seated in the bore and constantly urging the detent ball outwardly of the bore, and the handle having a pair of longitudinally spaced-apart detent pockets formed therein and alternately receiving the detent ball, thereby defining the alternate advanced and retracted positions of the guard on the handle.

7. A guarded skin hook for use during a surgical procedure, comprising a handle including a shank having a longitudinal axis and further having a pair of spaced-apart parallel hooks, one on each side of the longitudinal axis of the shank, a guard and means for slidably mounting the guard on the handle, including longitudinal flanges on the guard, and the handle having longitudinal guide tracks receiving the flanges on the guard, such that the guard has a longitudinal sliding movement on the handle, and such that the guard has a retracted position in which the hooks are exposed for use during the surgical procedure, and such that the guard further has an advanced position in which the hooks are substantially guarded, detent means between the guard and the handle, stop means independent of the detent means for limiting the sliding movement of the guard on the handle, the guard including a forward portion which is disposed below the hooks in the advanced position of the guard, and the forward portion of the guard having respective portions extending laterally beyond the hooks, thereby preventing accidental or inadvertent contact with the hooks in transferring the guarded skin hook from one health care provider to another during the surgical procedure.

8. A guarded skin hook for use during a surgical procedure, comprising a handle including a shank having at least one downwardly-projecting rearwardly-extending hook formed thereon, a guard and means for slidably mounting the guard on the handle for relative limited longitudinal movement thereon, the guard having a retracted position in which the hook is exposed for use during the surgical procedure, and the guard further having an advanced position in which the hook is substantially guarded, the guard including a forward portion which is disposed below the hook in the advanced position of the guard, and the forward portion of the guard having respective portions extending laterally beyond the hook, thereby preventing accidental or inadvertent contact with the hook in transferring the guarded skin hook from one health care provider to another during the surgical procedure, wherein the forward portion of the guard comprises a first section extending substantially perpendicular to the shank, and a second section formed integrally with the first section, projecting forwardly therefrom and substantially parallel to the shank, and being disposed below the hook in the advanced position of the guard.

9. A guarded skin hook for use during a surgical procedure, comprising a handle having a bottom portion and further having respective sides, each of which is provided with a guide track, a shank formed integrally within the handle and projecting forwardly thereof, the shank having at least one hook projecting downwardly therefrom, a guard having a pair of inturned flanges received in the respective guide tracks in the sides of the handle, thereby slidably mounting the guard on the handle for relative longitudinal movement thereon, stop means cooperating between the guard and the handle for limiting the longitudinal sliding movement of the guard on the handle, and spring-loaded detent means between the guard and the bottom portion of the handle, thereby defining a first position in which the guard is retracted on the handle and the hook is exposed for use of the guarded skin hook during the surgical procedure, and a second position in which the guard is advanced on the handle for substantially precluding inadvertent or accidental contact with the hook when the guarded skin hook is not being used or is being transferred from one health care provider to another.

10. The guarded skin hook of claim 9, wherein the guard has a forward portion disposed below the hook.

11. In a guarded skin hook having a handle and further having a downwardly and rearwardly projecting hook provided with a sharp point, the improvement comprising a guard to prevent inadvertent contact with the hook, means for slidably mounting the guard on the handle, said means including a pair of inturned laterally-extending flanges on the guard, and the handle having a pair of longitudinal guide tracks formed thereon and receiving the respective flanges on the guard, two-position spring-loaded detent means between the guard and the handle, the guard having a forwardmost substantially-flat portion disposed below the hook, extending laterally thereof, and terminating in a lateral edge, and the respective distances between the sharp point of the hook and the forwardmost substantially-flat portion of the guard precluding inadvertent contact with the hook.

12. A guarded skin hook, comprising a handle including a shank having a hook thereon, a guard disposed below the shank and slidably mounted on the handle for relatively limited longitudinal movement thereon, the guard having a retracted position in which the hook is exposed and further having an advanced position in which the hook is substantially guarded, the guard including a forwardmost portion disposed below the hook in the advanced position of the guard, the forwardmost portion of the guard being open above the hook and closed below the hook, the forwardmost portion further being substantially spoon-shaped and concave with respect to the hook and having respective side portions extending upwardly on either side of the hook, thereby preventing accidental or inadvertent contact with the hook when the hook is exposed, and spring-loaded detent means between the guard and the handle.

13. The guarded skin hook of claim 12, wherein the shank has a longitudinal axis, wherein the hook comprises a first hook disposed on one side of the longitudinal axis of the shank, and wherein a second hook extends from the shank and is disposed on the other side of the longitudinal axis, such that a pair of spaced-apart hooks is provided, one on each side of the longitudinal axis of the shank.

14. A guarded skin hook for use during a surgical procedure, comprising a handle, a shank integral with the handle and having a longitudinal axis, the shank further having at least one downwardly-projecting hook formed thereon, a guard, means for slidably mounting the guard on the handle, including a pair of inturned laterally-extending flanges on the guard, and the handle having a pair of longitudinal guide tracks formed thereon and receiving the respective flanges on the guard, such that the guard has a retracted position wherein the hook is exposed for use during the surgical procedure, and an advanced position wherein the hook is guarded against accidental or inadvertent contact, and the guard having an intermediate position between the advanced and retracted positions thereof, wherein the guard may contact the skin of the patient being engaged by the hook and clamp the patient's skin between the guard and the hook, thereby preventing the skin from tearing, slipping off, or otherwise becoming disengaged from the hook during use of the guarded skin hook.

15. The guarded surgical skin hook of claim 14, wherein the hook comprises a first hook disposed on one side of the longitudinal axis of the shank, and wherein a second hook extends from said shank, the hooks being spaced-apart and parallel to one another, such that a respective hook is disposed on each side of the longitudinal axis of the shank.

16. A guarded skin hook for use during a surgical procedure, comprising a handle, a shank integral with the handle and having a longitudinal axis, the shank further having at least one downwardly-projecting hook formed thereon, a guard, means for slidably mounting the guard on the handle for limited longitudinal movement thereon, such that the guard has a retracted position wherein the hook is exposed for use during the surgical procedure, and such that the guard has an advanced position wherein the guard prevents accidental or inadvertent contact with the hook, and the guard having an intermediate position between the advanced and retracted positions thereof, wherein the guard may contact the skin of the patient being engaged by the hook and clamp the patient's skin between the guard and the hook, thereby preventing the skin from tearing, slipping off, or otherwise becoming disengaged from the hook during use of the guarded skin hook, wherein the guard includes a forwardmost portion, the forwardmost portion being substantially concave with respect to the hook and having respective side portions extending substantially upwardly on either side of the hook, such that the forwardmost portion of the guard is open above the hook and closed below the hook.

17. The guarded skin hook of claim 14, further comprising a spring-loaded detent means formed between the handle and the guard for securing the guard in the respective retracted and advanced positions thereof, the detent means including a slide button mounted on the guard and disposed below the handle.

18. The guarded surgical skin hook of claim 17, wherein the spring-loaded detent means includes a spring-loaded detent carried by one of the handle and the guard, and a pair of longitudinally-spaced detent pockets formed in the other of the handle and the guard, such that when the guard is in the retracted and advanced positions thereof, the spring-loaded detent is urged into one of the respective detent pockets, whereby the guard is securely held in the respective retracted and advanced positions, and further such that when a user wishes to move the guard between the retracted and advanced positions thereof, the user needs only to move the guard for unseating the spring-loaded detent from the detent pockets therefor.

19. A guarded skin hook for use during a surgical procedure, comprising a handle, a shank integral with the handle and having a longitudinal axis, the shank further having at least one downwardly-projecting hook formed thereon, a guard, means for slidably mounting the guard on the handle for limited longitudinal movement thereon, such that the guard has a retracted position wherein the hook is exposed for use during the surgical procedure, and such that the guard has an advanced position wherein the guard prevents accidental or inadvertent contact with the hook, and the guard having an intermediate position between the advanced and retracted positions thereof, wherein the guard may contact the skin of the patient being engaged by the hook and clamp the patient's skin between the guard and the hook, thereby preventing the skin from tearing, slipping off, or otherwise becoming disengaged from the hook during use of the guarded skin hook, further including a spring-loaded detent means formed between the handle and the guard for securing the guard in the respective retracted and advanced portions thereof, wherein the spring-loaded detent means includes a spring-loaded detent carried by one of the handle and the guard, and a pair of longitudinally-spaced detent pockets formed in the other of the handle and the guard, such that when the guard is in the retracted and advanced positions thereof, the spring-loaded detent is urged into one of the respective detent pockets, whereby the guard is securely held in the respective retracted and advanced positions, and further such that when a user wishes to move the guard between the retracted and advanced positions thereof, the user needs only to move the guard for unseating the spring-loaded detent from the detent pockets.

20. A guardian skin hook for surgical use, comprising a handle, a shank integral with the handle, and having a longitudinal axis, the shank further having a pair of parallel spaced-apart hooks formed thereon opposite of the handle, such that a respective hook is disposed on each side of the longitudinal axis, the hooks extending substantially downwardly from the shank, a guard slidably mounted on the handle for limited longitudinal movement thereon, such that the guard has a retracted position, wherein the hooks are exposed for use during a surgical procedure, and an advanced position wherein the hooks are substantially guarded against inadvertent contact, the guard including a forwardmost portion which is substantially concave with respect to the hooks, the forwardmost portion having respective side portions which, when the guard is in the advanced position thereof, extend substantially upwardly on either side of the hooks, such that the forwardmost portion of the guard is open above the hooks and closed below the hooks, thereby preventing accidental or inadvertent contact with the hooks when the guard is disposed in the advanced position thereof, and the guard further being movable to at least one intermediate desired position between the advanced and retracted positions of the guard, whereby the guard may contact the skin of the patient being hooked by the hooks, such that the patient's skin is clamped between the guard and the hooks, thereby preventing the patient's skin from tearing, slipping off, or otherwise becoming disengaged from the hooks during use of the skin hook, spring-loaded detent means between the handle and the guard, and stop means between the handle and the guard, the stop means being independent of the detent means.

21. In a medical instrument, wherein a main body portion includes a forward end portion having a downwardly-projecting rearwardly-extending hook means formed thereon, the improvement comprising a guard, means for slidably mounting the guard on the main body portion such that the guard has an advanced position thereon in which the hook means is substantially guarded and further has a retracted position in which the hook means is exposed for use during a medical procedure, the means for slidably mounting the guard on the handle including a pair of inturned laterally-extending flanges on the guard, and the main body portion having a pair of longitudinal guide tracks formed thereon and receiving the respective flanges on the guard, two-position spring-loaded detent means between the guard and the main body portion, and the guard having a forwardly-extending downwardly-offset portion which is open above the hook means and closed below the hook means, whereby the guard prevents accidental or inadvertent contact with the hook means when the medical instrument is being transferred from one health care provider to another during a medical procedure.

22. The improvement of claim 21, wherein the medical instrument comprises a skin hook.

23. The improvement of claim 21, wherein the medical instrument comprises a surgical pick.

24. The improvement of claim 21, wherein the medical instrument comprises a dental scaler.

25. The improvement of claim 21, wherein the medical instrument comprises a periodontal scaler.

26. The method of using a surgical instrument following an incision on a patient, wherein the instrument has at least one hook thereon, and wherein a guard is carried by the instrument, the guard having a retracted position in which the hook is exposed and further having an advanced position in which the hook is substantially covered against inadvertent or accidental contact, comprising the steps of retracting the guard to expose the hook, inserting the hook of the instrument into the incision on the patient, moving the guard back towards the hook, such that the skin is substantially clamped between the hook and the guard and does not slip off the hook, and moving the instrument away from the incision to peel away the skin from the incision.

27. The method of claim 26, wherein the instrument comprises a skin hook.

28. A guarded skin hook for use during a surgical procedure, wherein the guarded skin hook is received by a health care provider during the surgical procedure, comprising a substantially flat handle having respective sides, each of which is provided with a longitudinal guide track, a shank extending forwardly of the handle and having a downwardly-extending rearwardly-projecting hook formed thereon, a guard having a pair of longitudinal flanges received in the respective guide tracks in the sides of the handle, two-position spring-loaded detent means between the guard and the handle, thereby defining an advanced position in which the guard prevents inadvertent or accidental contact with the hook, and a retracted position in which the hook is exposed for use during the surgical procedure, the detent means including a detent button carried by the guard and disposed below the handle, and the handle having a top portion provided with ridge means thereon, such that the health care provider receiving the guarded skin hook will know intuitively the position of the guard and the relative orientation of the guarded skin hook from the tactile "feel" thereof.

29. The method of using a surgical instrument following an incision on a patient, wherein the instrument has at least one hook thereon, and wherein a guard is slidably carried by the instrument, the guard having a retracted position in which the hook is exposed and further having an advanced position in which the hook is substantially covered against inadvertent or accidental contact, comprising the steps of slidably retracting the guard to expose the hook, inserting the hook of the instrument into the incision on the patient, slidably moving the guard back towards the hook, such that the skin is substantially clamped between the hook and the guard and does not slip off the hook, and moving the instrument away from the incision to peel away the skin from the incision.

* * * * *